United States Patent
Piscitelli et al.

(10) Patent No.: US 12,102,638 B2
(45) Date of Patent: Oct. 1, 2024

(54) USE OF VIBEGRON TO TREAT OVERACTIVE BLADDER

(71) Applicant: Urovant Sciences GmbH, Basel (CH)

(72) Inventors: Stephen C. Piscitelli, Hillsborough, NC (US); Paul Mudd, Cary, NC (US)

(73) Assignee: Urovant Sciences GmbH, Basel (CH)

( * ) Notice: Subject to any disclaimer, the term of this patent is extended or adjusted under 35 U.S.C. 154(b) by 655 days.

(21) Appl. No.: 16/620,179

(22) PCT Filed: Jun. 6, 2018

(86) PCT No.: PCT/IB2018/054069
§ 371 (c)(1),
(2) Date: Dec. 6, 2019

(87) PCT Pub. No.: WO2018/224989
PCT Pub. Date: Dec. 13, 2018

(65) Prior Publication Data
US 2021/0077495 A1    Mar. 18, 2021

Related U.S. Application Data

(60) Provisional application No. 62/637,961, filed on Mar. 2, 2018, provisional application No. 62/635,146, filed on Feb. 26, 2018, provisional application No. 62/515,996, filed on Jun. 6, 2017.

(51) Int. Cl.
| | | |
|---|---|---|
| *A61K 31/519* | (2006.01) | |
| *A61K 9/00* | (2006.01) | |
| *A61K 9/20* | (2006.01) | |
| *A61K 9/28* | (2006.01) | |
| *A61P 13/10* | (2006.01) | |

(52) U.S. Cl.
CPC .......... *A61K 31/519* (2013.01); *A61K 9/0053* (2013.01); *A61K 9/2018* (2013.01); *A61K 9/2054* (2013.01); *A61K 9/2833* (2013.01); *A61P 13/10* (2018.01)

(58) Field of Classification Search
CPC .. A61K 31/519; A61K 9/0053; A61K 9/2018; A61K 9/2054; A61K 9/2833; A61P 13/10
See application file for complete search history.

(56) References Cited

U.S. PATENT DOCUMENTS

| | | | |
|---|---|---|---|
| 6,251,925 | B1 | 6/2001 | Donaldson et al. |
| 6,346,532 | B1 | 2/2002 | Maruyama et al. |
| 6,525,202 | B2 | 2/2003 | Hu et al. |
| 6,562,375 | B1 | 5/2003 | Sako et al. |
| 7,342,117 | B2 | 3/2008 | Kawazoe et al. |
| 7,396,958 | B2 | 7/2008 | Courtemanche et al. |
| 7,982,049 | B2 | 7/2011 | Kawazoe et al. |
| 8,247,415 | B2 | 8/2012 | Berger et al. |
| 8,399,480 | B2 | 3/2013 | Berger et al. |
| 8,415,126 | B2 | 4/2013 | Mundorff et al. |
| 8,642,661 | B2 | 2/2014 | Caltabiano et al. |
| 8,653,260 | B2 | 2/2014 | Berger et al. |
| RE44,872 | E | 4/2014 | Takasu et al. |
| 8,748,143 | B2 | 6/2014 | Liang et al. |
| 8,748,433 | B2 | 6/2014 | Berger et al. |
| 8,772,315 | B2 | 7/2014 | Suzuki et al. |
| 8,835,474 | B2 | 9/2014 | Takasu et al. |
| 9,522,129 | B2 | 12/2016 | Caltabiano et al. |
| 9,809,536 | B2 | 11/2017 | Chung et al. |
| 9,822,121 | B2 | 11/2017 | Chung et al. |
| 9,907,767 | B2 | 3/2018 | Caltabiano et al. |
| 9,956,194 | B2 | 5/2018 | Ohlstein et al. |
| 10,065,922 | B2 | 9/2018 | Stevens et al. |
| 10,087,189 | B2 | 10/2018 | Chung et al. |
| 10,287,289 | B2 | 5/2019 | Xu et al. |
| 10,350,182 | B2 | 7/2019 | Caltabiano et al. |
| 10,435,410 | B2 | 10/2019 | Chung et al. |
| 10,577,316 | B2 | 3/2020 | Chung et al. |
| 10,696,681 | B2 | 6/2020 | Xu et al. |
| 10,899,771 | B2 | 1/2021 | Chung et al. |
| 11,091,493 | B2 | 8/2021 | Xu et al. |
| 11,124,478 | B2 | 9/2021 | Chung et al. |
| 11,649,243 | B2 | 5/2023 | Xu et al. |
| 11,708,371 | B2 | 7/2023 | Chung et al. |
| 11,767,292 | B2 | 9/2023 | Chung et al. |
| 2012/0202819 | A1 | 8/2012 | Edmondson et al. |

(Continued)

FOREIGN PATENT DOCUMENTS

| | | | |
|---|---|---|---|
| JP | 2016503001 | A | 2/2016 |
| WO | WO 2003/072572 | A1 | 9/2003 |

(Continued)

OTHER PUBLICATIONS

Goodman and Gilman's The Pharmacological Basis of Therapeutics (Tenth Edition (2001), McGraw Hill, Chapter I, pp. 3-29.*
Di Salvo et al., "Pharmacological Characterization of a Novel Beta 3 Adrenergic agonist, Vibegron: Evaluation of Antimuscarinic Receptor Selectivity for Combination Therapy for Overactive Bladder," *J. Pharmacol. Exp. Ther.* 340, 2017, pp. 345-355.
Dong et al., "Convenient Synthesis of Homoproparglyglycine,," *Journal of Peptide Science*, 2008, pp. 1148-1150, vol. 14.
International Search Report for International Application No. PCT/US2014/023858, dated Jun. 6, 2014, 3 pages.
Xu, et al., "Asymmetric Synthesis of cis-2,5-Disubstituted Pyrrolidine, the Core Scaffold of Beta-3-AR Agonists," *Organic Letters*, 2013, pp. 1342-1345, vol. 15 No. 6.

(Continued)

*Primary Examiner* — Alicia L Otton
(74) *Attorney, Agent, or Firm* — Sterne, Kessler, Goldstein & Fox P.L.L.C.

(57) ABSTRACT

The present disclosure is directed to a method of treating overactive bladder comprising orally administering to a subject in need thereof an amount of from about 60 mg to about 90 mg (e.g., about 75 mg) of vibegron per day. The present disclosure is also directed to a pharmaceutical unit dosage composition comprising from about 60 mg to about 90 mg (e.g., about 75 mg) of vibegron for oral administration.

54 Claims, 2 Drawing Sheets

(56) References Cited

U.S. PATENT DOCUMENTS

| | | | |
|---|---|---|---|
| 2015/0087832 | A1 | 3/2015 | Chung et al. |
| 2017/0035716 | A1 | 2/2017 | Ohlstein et al. |
| 2017/0348263 | A1 | 12/2017 | Ohlstein et al. |
| 2017/0348288 | A1 | 12/2017 | Ohlstein et al. |
| 2018/0147169 | A1 | 5/2018 | Caltabiano et al. |
| 2019/0083433 | A1 | 3/2019 | Ohlstein et al. |
| 2019/0083434 | A1 | 3/2019 | Ohlstein et al. |
| 2020/0290962 | A1 | 9/2020 | Chung et al. |
| 2020/0392141 | A1 | 12/2020 | Xu et al. |
| 2021/0077493 | A1 | 3/2021 | Piscitelli et al. |
| 2021/0221815 | A1 | 7/2021 | Chung et al. |
| 2022/0073459 | A1 | 3/2022 | Chung et al. |
| 2022/0073523 | A1 | 3/2022 | Xu et al. |
| 2022/0117971 | A1 | 4/2022 | Mudd et al. |
| 2023/0027066 | A1 | 1/2023 | Mudd |
| 2023/0218624 | A1 | 7/2023 | Piscitelli et al. |
| 2024/0050457 | A1 | 2/2024 | Mudd |

FOREIGN PATENT DOCUMENTS

| | | | |
|---|---|---|---|
| WO | WO2004098586 | A1 | 11/2004 |
| WO | WO2008128968 | A1 | 10/2008 |
| WO | WO 2009/124166 | A1 | 10/2009 |
| WO | WO 2009/124167 | A1 | 10/2009 |
| WO | WO 2011/043942 | A1 | 4/2011 |
| WO | WO 2013/062878 | A1 | 5/2013 |
| WO | WO 2013/062881 | A1 | 5/2013 |
| WO | WO 2013/074650 | A1 | 5/2013 |
| WO | WO2013092918 | A1 | 6/2013 |
| WO | WO2014091368 | A1 | 6/2014 |
| WO | WO2014/150639 | A1 | 9/2014 |
| WO | WO2017/070689 | A2 | 4/2017 |
| WO | WO2017/210696 | A1 | 12/2017 |
| WO | WO2018/224990 | A1 | 12/2018 |
| WO | WO2019/124507 | A1 | 6/2019 |
| WO | WO2019/224788 | A1 | 11/2019 |
| WO | WO2020/115705 | A1 | 6/2020 |
| WO | WO2020/188505 | A1 | 9/2020 |
| WO | WO2022137178 | A1 | 6/2022 |
| WO | WO2022175848 | A1 | 8/2022 |

OTHER PUBLICATIONS

Whisstock, et al., "Prediction of Protein Function from Protein Sequence and Structure," *Quarterly Reviews of Biophysics* 2003, vol. 36 (3): 307-340.

Witkowski, et al., "Conversion of a Beta-Ketoacyl Synthase to a Malonyl Decarboxylase by Replacement of the Active-Site Cysteine with Glutamine," *Biochemistry* 38:11643-11650, 1999.

Kisselev, L., "Polypeptide Release Factors in Prokaryotes and Eukaryotes: Same Function, Different Structure," *Structure* 2002, vol. 10: 8-9.

Ebenezer, W.J. and Wight, P., "Ketones: a,i3-Unsaturated Ketones," in *Comprehensive Organic Functional Group Transformations*, vol. 3, Katritzky, A.R., et al., eds., pp. 205-276, Elsevier Ltd., England (1995).

Extended European Search Report for EP Application No. 14768236.3, Munich, Germany, dated Nov. 28, 2016, 7 pages.

International Preliminary Report on Patentability and Written Opinion for International Application No. PCT/US2014/023858, The International Bureau of WIPO, Geneva, Switzerland, dated Sep. 15, 2015, 5 pages.

Koszelewski, D., et at., "Immobilization of w-transaminases by encapsulation in a solgel/ celite matrix," *Journal of Molecular Catalysis B: Enzymatic* 63:39-44, Elsevier B.V., Netherlands (2010).

Martin, A.R., et al., "Characterization of Free and Immobilized (S)-Aminotransferase for Acetophenone Production," *Applied Microbiology and Biotechnology* 76(4):843-851, Springer International, Germany (2007).

Mateo, C., et al., "Epoxy Sepabeads: A Novel Epoxy Support for Stabilization of Industrial Enzymes via Very Intense Multipoint Covalent Attachment," *Biotechnology Progress* 18(3):629-634, American Chemical Society and American Institute of Chemical Engineers, United States (2002).

North, M., "Nitriles: General Methods and Aliphatic Nitriles," in *Comprehensive Organic Functional Group Transformations*, vol. 3, Katritzky, A.R., et al., eds., pp. 611-640, Elsevier Ltd., England (1995).

Parkes, K.E.B. and Richardson, S.K., "Ketones: Dialkyl Ketones," in *Comprehensive Organic Functional Group Transformations*, vol. 3, Katritzky, A.R., et at., eds., pp. 111-204, Elsevier Ltd., England (1995).

Sonogashira, K., "Palladium-Catalyzed Alkynylation: Sonogashira Alkyne Synthesis," in *Handbook of Organopalladium Chemistry for Organic Synthesis*, Negishi, E-1., ed., pp. 493-529, John Wiley & Sons, Inc., United States (2002).

Truppo, M.D. and Hughes, G., "Development of an Improved Immobilized CAL-B for the Enzymatic Resolution of a Key Intermediate to Odanacatib," *Organic Process Research & Development* 15(5):1033-1035, American Chemical Society, United States (2011).

Yi, S.S., et al., "Covalent Immobilization of w-transaminase from Vibrio fluvia/is JS17 on chitosan beads," *Process Biochemistry* 42(5):895-898, Elsevier Ltd., England (2007).

International Preliminary Report on Patentability and Written Opinion for International Application No. PCT/US2009/039249, The International Bureau of WIPO, Geneva, Switzerland, dated Oct. 5, 2010, 6 pages.

International Preliminary Report on Patentability and Written Opinion for International Application No. PCT/US2009/039253 The International Bureau of WIPO, Geneva, Switzerland, dated Oct. 5, 2010, 5 pages.

International Search Report for International Application No. PCT/US2009/039249, European Patent Office, Netherlands, dated Aug. 31, 2009, 4 pages.

International Search Report for International Application No. PCT/US2009/039253, European Patent Office, Netherlands, dated Jun. 17, 2009, 3 pages.

International Search Report for International Application No. PCT/US2012/061252, European Patent Office, Netherlands, dated Jan. 18, 2013, 2 pages.

Adkins H et al. The preparation of Raney Nickel catalysts and their use under conditions comparable with those for platinum and palladium catalysts. 1948. Contribution from the Laboratory of Organic Chemistry, University of Wisconsin. 695-698.

Hultin PG. A Guide to Solvents and Reagents in Introductory Organic Chemistry for students in 2.222. 2002. p. 1-17.

Morriello, Design of a novel pyrrolidine scaffold utilized in the discovery of potent and selective human beta 3adrenergic receptor agonists, Bioorganic & Medicinal Chemistry Letters, 2011, 1865-1870, 21 (6).

Extended European Search Report for 12842776.2, dated Mar. 12, 2015; 4 pages.

Haynes, W.M., "Dissociation Constants of Organic Acids and Bases," in *CRC Handbook of Chemistry and Physics*, 92nd Edition, Haynes, W.M., et al., eds., Section 5, pp. 94-103, Taylor & Francis Group, United States (2011).

Huisman, G.W., et al., "Practical chiral alcohol manufacture using ketoreductases," *Current Opinion in Chemical Biology* 14:1-8, Elsevier Ltd., England (2010).

Kaiser, H-P. and Muchowski, J.M., "Catalytic Hydrogenation of Pyrroles at Atmospheric Pressure," *Journal of Organic Chemistry* 49(2):4203-4209, American Chemical Society, United States (1984).

Wuts, P.G.M., "The Role of Protective Groups in Organic Synthesis," in *Greene's Protective Groups in Organic Synthesis*, Fourth Edition, Wuts, P.G.M. and Greene, T.W., eds., Chapter 1, pp. 1-15, John Wiley & Sons, Inc., United States (2007).

Devos, D. and Valencia, A., "Practical limits of function prediction," *Proteins: Structure, Function, and Genetics* 41:98-107, Wiley-Liss, Inc., United States (2000).

International Preliminary Report on Patentability and Written Opinion for International Application No. PCT/US2012/061249, The International Bureau of WIPO, Geneva, Switzerland, dated Apr. 29, 2014, 4 pages.

(56) References Cited

OTHER PUBLICATIONS

International Search Report for International Application No. PCT/US2012/061249, European Patent Office, Netherlands, dated Dec. 8, 2012, 2 pages.
Extended European Search Report dated Dec. 18, 2019, in European Patent Application 19184972.8, 7 pages.
Co-pending Application, U.S. Appl. No. 17/155,982, Inventors, Chung, Y.Y.I., et al. filed on Jan. 22, 2021 (Not Published).
Co-pending Application, U.S. Appl. No. 17/057,554, Inventors, Mudd Jr., P.N et al. filed on Nov. 20, 2020 (Not Published).
International Preliminary Report on Patentability and Written Opinion for International Application No. PCT/IB2018/054069, The International Bureau of WIPO, Geneva, Switzerland, dated Dec. 10, 2019, 7 pages.
International Preliminary Report on Patentability and Written Opinion for International Application No. PCT/IB2018/054070, The International Bureau of WIPO, Geneva, Switzerland, dated Dec. 10, 2019, 7 pages.
Yoshida, M. et al., "Vibegron,a novel potent and selective beta3-adrenoreceptor agonist, for the treatment of patients with overactive bladder: A randomized, couble-blind, placebo-controlled phase 3 study," *Eur Urol Suppl* 2018, 17(2); e1531-e1532.
Mitcheson, D. et al., "Once Daily Vibegron Improves Quality of Life Measures in Patients with Overactive Bladder," *Value in Health*, 21 (2018) S267-S268.
International Search Report for International Application No. PCT/IB2018/054069, European Patent Office, NL, dated Sep. 24, 2018, 3 pages.
ClinicalTrials.gov Protocol Registration Preview for MK-4618-008 CSP (A Study of the Efficacy and Safety of Vibegron (MK-4618) in Participants with Overactive Bladder (OAB); Indicating first posted Mar. 15, 2011.
ClinicalTrials.gov Protocol Registration Preview for MK-4618-004 CSP (A Study of the Pharmacokinetics and Pharmacodynamics of Vibegron (MK-4618) in Women With Overactive Bladder; Indicating first posted Dec. 28, 2011.
ClinicalTrials.gov Protocol Registration Preview for MK-4618-014 CSP (Single-Dose Study of the Pharmacokinetics of Vibegron (MK-4618) in Participants with Renal Insufficiency; Indicating first posted Jun. 26, 2012.
ClinicalTrials.gov Protocol Registration Preview for MK-4618-013 CSP (Single-Dose Study of the Pharmacokinetics of Vibegron (MK-4618) in Adults with Hepatic Insufficiency; Indicating first posted Nov. 29, 2012.
ClinicalTrials.gov Protocol Registration Preview for RVT-901-3003 (An International Phase 3, Randomized, Double-Blind, Placebo- and Active (Tolterodine)-Controlled Multicenter Study to Evaluate the Safety and Efficacy of Vibegron in Patients with Symptoms of Overactive Bladder); Indicating first posted Apr. 10, 2018.
Yoshida, M., et al., "Vibegron, a Novel Potent and Selective β3-Adrenoreceptor Agonist, for the Treatment of Patients with Overactive Bladder: A Randomized, Double-Blind, Placebo-Controlled Phase 3 Study," *European Urology* 73 (2018) 783-790.
Yoshida, M., et al., "Long-Term Safety and Efficacy of the Novel β3-Adrenoreceptor Agonist Vibegron in Japanese Patients with Overactive Bladder: A Phase III Prospective Study," Int. J. of Urology (2018), 25, 668-675.
Edmondson, S.D. et al., "Discovery of Vibegron: A Potent and Selective ß3 Adrenergic Receptor Agonist for the Treatment of Overactive Bladder," *Journal of Medicinal Chemistry*, 2016, 59(2), 609-623.
Xu, Feng et al., "Green by Design for Process Evolution: Asymmetric Syntheses of Vibegron," Abstracts of Papers, Past and Present Research Systems of Green Chemistry, Orlando, Sep. 14-16, 2015.
Edmondson, S. et. al., "Discovery and Early Development of Vibegron (MK-4618) : A Potent and Selective β3-AR Agonist for the Treatment of Overactive Bladder," Abstracts of Papers, 249th ACS Natl. Mtg. & Expo. Denver, CO Mar. 22-26, 2015.

Giarenis, I. et al., "Overactive Bladder and the β3-Adrenoceptor Agonists: Current Strategy and Future Prospects," Drugs, (Sep. 1, 2015) vol. 75, No. 15, pp. 1707-1713.
Zhu, C. et al., "Discovery of Benzamides as Potent Human β3 Adrenergic Receptor Agonists," *Bioorganic and Medicinal Chemistry Letters*, (Jan. 1, 2016) vol. 26, No. 1, pp. 55-59.
Perabo, F. G. E. et al., "Drug Development for LUTS—The Challenge for Industry," *Drug Discovery Today: Therapeutic Strategies*, (Spring 2012) vol. 9, No. 1, pp. e5-e14.
Polland, A., et al., "Emerging Treatments for Urinary Incontinence," Expert Opinion Emerg. Drugs (19, No. 2, 281-290, 2014).
International Search Report for International Application No. PCT/US2010/50328, United States Patent Office, dated Nov. 18, 2010, 2 pages.
International Preliminary Report on Patentability and Written Opinion for International Application No. PCT/US2010/050328, The International Bureau of WIPO, Geneva, Switzerland, dated Apr. 11, 2012, 7 pages.
International Preliminary Report on Patentability and Written Opinion for International Application No. PCT/US2012/061252, The International Bureau of WIPO, Geneva, Switzerland, dated Apr. 29, 2014, 4 pages.
Office Action dated Nov. 17, 2011, in U.S. Appl. No. 12/417,239, filed Apr. 2, 2009, Inventor, Berger, R., 5 pages.
Office Action dated Feb. 1, 2012, in U.S. Appl. No. 12/936,221, filed Oct. 4, 2010, Inventor, Berger, R., 4 pages.
Office Action dated Mar. 26, 2013 in U.S. Appl. No. 13/527,934, filed Jun. 20, 2012, Inventor, Berger, R., 6 pages.
Office Action dated Jun. 21, 2013 in U.S. Appl. No. 13/527,934, filed Jun. 20, 2012, Inventor, Berger, R., 6 pages.
Office Action dated Aug. 17, 2017 in U.S. Appl. No. 14/776,366, filed Sep. 14, 2015, Inventor, Su, F., 15 pages.
Office Action dated May 21, 2015 in U.S. Appl. No. 14/354,158, filed Apr. 25, 2014, Inventor, Chung, J.Y., 8 pages.
Office Action dated Nov. 10, 2015 in U.S. Appl. No. 14/354,158, filed Apr. 25, 2014, Inventor, Chung, J.Y., 10 pages.
Office Action dated Apr. 19, 2017 in U.S. Appl. No. 15/057,427, filed Mar. 1, 2016, Inventor, Chung, J.Y., 8 pages.
Office Action dated Jan. 3, 2018 in U.S. Appl. No. 15/808,740, filed Nov. 9, 2017, Inventor, Chung, J.Y., 8 pages.
Office Action dated Feb. 7, 2019 in U.S. Appl. No. 16/133,320, filed Sep. 17, 2018, Inventor, Chung, J.Y., 5 pages.
Office Action dated Jun. 2, 2020 in U.S. Appl. No. 16/890,180, filed Oct. 1, 2019, Inventor, Chung, J.Y., 8 pages.
Office Action dated Jun. 24, 2019 in U.S. Appl. No. 15/715,493, filed Sep. 26, 2017, Inventor, Chung, J.Y., 6 pages.
International Search Report for International Application No. PCT/IB2018/054070, European Patent Office, NL, dated Sep. 24, 2018, 3 pages.
"Hypertension in America: A National Reading," *Am. J. Manag. Care*, 2005, vol. 11, No. 13, Sup. pp. S383-S385.
Benner, J.S. et al., "Patient-reported reasons for discontinuing overactive bladder medication," *BJUI International*, 2009, vol. 105, pp. 1276-1282.
Wagg, A. et al., "Persistence and adherence with the new beta-3 receptor agonist, mirabegron, versus antimuscarinics in overactive bladder: Early experience in Canada," *Can. Urol. Assoc. J.* 2015, vol. 9, pp. 343-350.
"Myrbetriq: Highlights of Prescribing Information," Astellas Pharma, Jun. 2012, 23 pages.
"Gemtesa: Highlights of Prescribing Information," Urovant Sciences GmbH, Dec. 2020, 14 pages.
Office Action dated Jun. 24, 2022 in U.S. Appl. No. 16/620,192, filed Dec. 6, 2019, Inventors Piscitelli, S. C., et al., 9 pages.
Co-pending Application, U.S. Appl. No. 18/049,200, Inventors Piscitelli, S. C., et al., filed on Oct. 24, 2022 (Not Published).
Office Action dated Aug. 16, 2022 in U.S. Appl. No. 17/155,982 Chung, J.Y.L, et al., filed Jan. 22, 2021, 9 pages.
Office Action dated Aug. 18, 2022 in U.S. Appl. No. 17/399,274 XU, Feng, et al., filed Aug. 11, 2021, 6 pages.
Badlani, G., "Overactive Bladder: Advancement or More of the Same," European Urology 73(5): 791-792 (Editorial) (Supplementary Data), Elsevier, Netherlands (May 2018).

(56) References Cited

OTHER PUBLICATIONS

Office Action mailed Jan. 19, 2023 in U.S. Appl. No. 17/478,601, filed Sep. 17, 2021, Inventors Chung, J. Y.L., et al., 8 pages.

"Administrative and Correspondence Documents," Center for Drug Evaluation and Research Application No. 213006Orig1s000, Jan. 19, 2021.

"Clinical Pharmacology Review(s)," Center for Drug Evaluation and Research Application No. 213006Orig1s000, Dec. 23, 2020.

D'Souza, A.O., et al. "Persistence, adherence, and switch rates among extended-release and immediate-release overactive bladder medications in a regional managed care plan," *J. Manag. Care Pharm.* 2008; 14(3): 291-301.

Greenland, S., et al. "Estimation of a common effect parameter from sparse follow-up data," *Biometrics* 1985;41(1):55-68.

Hallas, J., et al. "Incidence of cardiovascular events in new users of overactive bladder medications in Denmark," Abstracts of the 32nd International Conference on Pharmacoepidemiology & Therapeutic Risk Management. Dublin, Ireland. Aug. 25-28, 2016. Abstract 848. *Pharmacoepidemiol Drug Saf.* 2016; 25(S3):492.

Rosa G.M., et al. "Cardiovascular Safety of B3-adrenoceptor Agonists for the Treatment of Patients with Overactive Bladder Syndrome," Eur Urol. Feb. 2016;69(2):311-23.

Takeda H, et al. "Effects of ß3-adrenoceptor stimulation on prostaglandin E2-induced bladder hyperactivity and on the cardiovascular system in conscious rats," *Neurology and Urodynamics* 2002; 21: 558-65.

Co-pending Application, United States U.S. Appl. No. 18/546,585, Inventor, Zhou, J.., filed on Feb. 16, 2022 (Not Published).

U.S. Appl. No. 18/258,953 Co-pending Application, U.S. Appl. No. 18/258,953, Inventor, Mudd, P.N. filed on Dec. 22, 2021 (Not Published).

Co-pending Application, U.S. Appl. No. 18/508,594, Inventors, Xu, F. et al. filed on Nov. 14, 2023 (Not Published).

Yamaguchi, O. et al., "Phase III Study to Assess Long-Term (52-Week) Safety and Efficacy of Mirabegron, a B3-Adrenoceptor Agonist, in Japanese Patients with Overactive Bladder," *LUTS* 2017: 9; 38-45.

"An International Phase 3, Randomized, Double-Blind, Placebo- and Active (Tolterodine)-Controlled Multicenter Study to Evaluate the Safety and Efficacy of Vibegron in Patients with Symptoms of Overactive Bladder," Protcol RVT-901-3003; Nov. 15, 2018; Retrieved from:https://clinicaltrials.gov/study/NCT03492281?term=vibegron&rank=8.

"A Single Dose Study to Assess the Effect of MK-4618 on QTc Interval," Clinical Study Report, P012V01, Feb. 17, 2015.

"A Single Dose Study to Assess the Effect of MK-4618 on QTc Interval," Protocol, Jan. 8, 2013.

NDA 213006: Section 2.7.4: Summary of Clinical Safety (Table of Contents, §§ 1.1.3.1, 1.1.3.2, 1.1.3.4, 1.1.3.5, 1.1.4, 1.1.5, and 4.1) Submitted Dec. 26, 2019.

NDA 213006: Section 2.5: Clinical Overview (Table of Contents, pp. 7-9, and §§5, §.1, 5.2, 5.3, 6.3, and 6.4) Submitted Dec. 26, 2019.

Vibegron IND106410 Type B EOP2 Meeting Background Materials (Table of Contents, pp. 26-28, §10.7.1, and Appendix 4: "Summary of Jan. 18, 2013 Type B BOP2 Meeting Comments and Current Urovant Position") (Jun. 23, 2017).

\* cited by examiner

USE OF VIBEGRON TO TREAT OVERACTIVE BLADDER

BACKGROUND

Overactive bladder (OAB) is a chronic and sometimes debilitating condition of the lower urinary tract. The function of the lower urinary tract is to store and periodically release urine. This requires the orchestration of storage and micturition reflexes which involve a variety of afferent and efferent neural pathways, leading to modulation of central and peripheral neuroeffector mechanisms, and resultant coordinated regulation of sympathetic and parasympathetic components of the autonomic nervous system as well as somatic motor pathways. These proximally regulate the contractile state of bladder (detrusor) and urethral smooth muscle, and urethral sphincter striated muscle.

Overactive bladder, from a pathophysiologic perspective, has been linked with detrusor overactivity. OAB is characterized by the symptoms of urinary urgency, with or without urgency urinary incontinence, usually associated with frequency and nocturia. The prevalence of OAB in the United States and Europe has been estimated at 16 to 17% in both women and men over the age of 18 years. Overactive bladder is most often classified as idiopathic, but can also be secondary to neurological condition, bladder outlet obstruction, and other causes.

Currently, the predominant class of drugs used to treat OAB is antimuscarinics. The clinical use of antimuscarinics is limited by modest efficacy and poor tolerability due to mechanism-based side effects including dry mouth, constipation and the potential for CNS adverse effects (e.g., cognitive impairment). High discontinuation rates have been observed for both tolterodine and oxybutynin, two commonly prescribed antimuscarinics, in both clinical trials and real-world settings.

Beta-3 adrenergic receptor ($\beta_3$-AR) activation is an effective way of relaxing the detrusor in normal and pathogenic states. Functional evidence in support of an important role for the $\beta_3$-AR in urine storage emanates from studies in vivo. $\beta_3$-AR agonists have demonstrated efficacy in alleviating symptoms of OAB. To date, only one $\beta_3$-AR agonist, mirabegron (Astellas Pharma Global Development, Inc), has received marketing approval in the US and Japan for the treatment of OAB. Mirabegron activates the $\beta_3$-AR in the detrusor muscle in the bladder, which leads to muscle relaxation and an increase in bladder capacity. Reductions in micturition frequency, urinary incontinence and urgency episodes, and increases in mean volume voided per micturition were observed with mirabegron Vibegron, (6S)—N-[4-[[(2S,5R)-5-[(R)-hydroxy(phenyl) methyl]pyrrolidin-2-yl]methyl]phenyl]-4-oxo-7,8-dihydro-6H-pyrrolo[1,2-a]pyrimidine-6-carboxamide, is a potent and highly selective beta-3 adrenergic receptor ($\beta_3$-AR) agonist demonstrating >9,000 fold selectivity for activation of $\beta_3$-AR over $\beta_2$-AR and $\beta_1$-AR in cell based in vitro assays. See Edmondson et al., J. Med. Chem. 59:609-623 (2016).

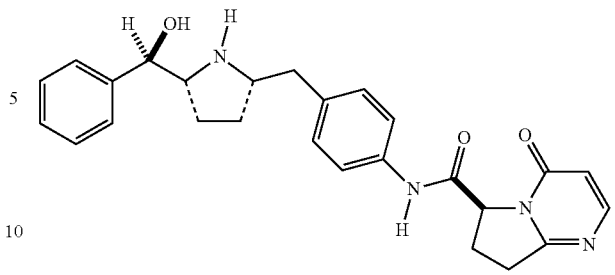

Vibegron is disclosed as a $\beta_3$-AR agonist in U.S. Pat. Nos. 8,399,480 and 8,247,415. Synthetic methods for preparing vibegron are disclosed in United States Publication Nos. US 2017/0145014, US 2015/0087832, US 2016/0176884 and US 2014/0242645. All of the cited publications are herein incorporated by reference in their entireties.

SUMMARY

Figure 1:
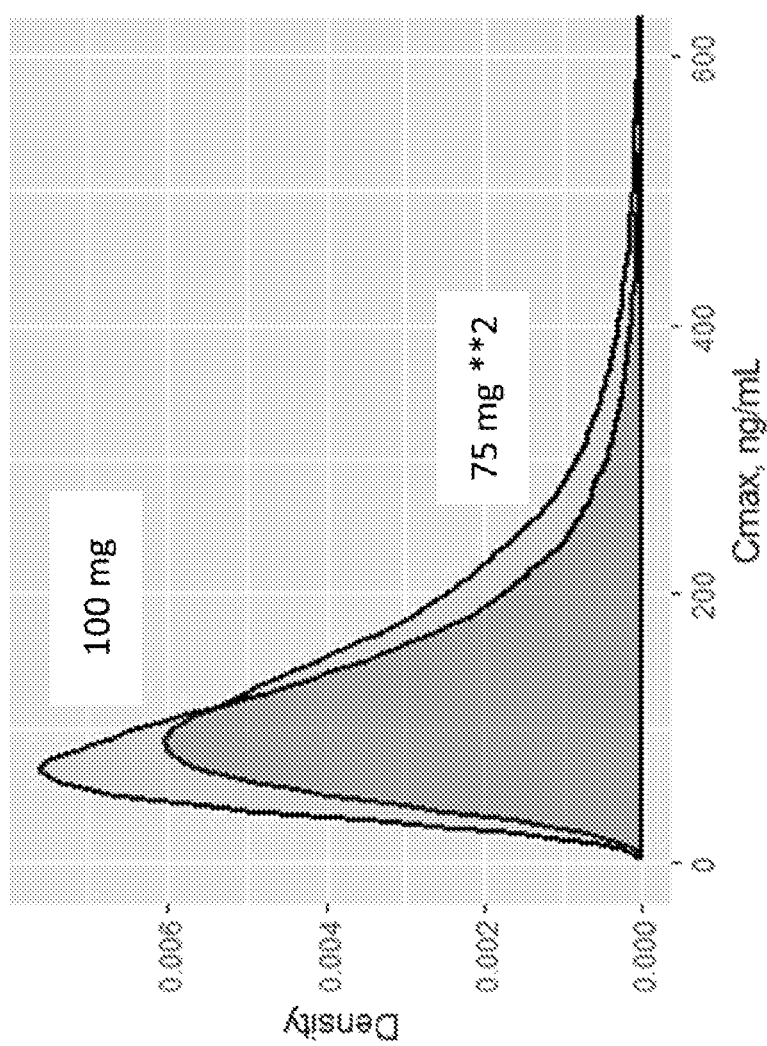
FIG. 1 depicts an overlay of density plots of exposure with vibegron 100 mg and 75 mg, as estimated in special populations.

The present disclosure provides a method of treating overactive bladder, the method comprising orally administering to a subject in need thereof an amount of from 60 mg to 90 mg of vibegron per day.

The present disclosure further provides a pharmaceutical unit dosage composition comprising from 60 mg to 90 mg vibegron, wherein the unit dosage composition is suitable for oral administration.

DETAILED DESCRIPTION

In order that the present disclosure can be more readily understood, certain terms are first defined. As used in this application, except as otherwise expressly provided herein, each of the following terms shall have the meaning set forth below. Additional definitions are set forth throughout the application.

In this specification and the appended claims, the singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related.

The term "about" as used in connection with a numerical value throughout the specification and the claims denotes an interval of accuracy, familiar and acceptable to a person skilled in the art. Such interval of accuracy is ±10%.

The term "overactive bladder" generally refers to a clinical syndrome characterized by urinary urgency, with or without urge incontinence, optionally associated with frequency and nocturia.

The term "urgency urinary incontinence" (UUI) as used herein means an involuntary loss of urine accompanied by a strong, sudden need to urinate and can be used interchangeably with "urge urinary incontinence" or "urge incontinence." UUI is distinguished from stress urinary incontinence, which is the involuntary loss of urine on effort or physical exertion (e.g., sporting activities), or on sneezing or coughing.

The term "impairment" as used herein means acute or chronic reduction in function. For example, renal impairment refers to a medical condition where the kidneys fail to maintain their normal function, so that waste products and metabolites accumulate in the blood.

The term "urinary urgency" as used herein means a sudden compelling desire to urinate which is difficult to defer.

The term "urinary frequency" as used herein refers to a need for frequent emptying of the bladder.

The term "free base" as used herein refers to a basic chemical compound itself, not in the form of a salt. For example, vibegron free base refers to (6S)—N-[4-[[(2S,5R)-5-[(R)-hydroxy(phenyl)methyl]pyrrolidin-2-yl]methyl]phenyl]-4-oxo-7,8-dihydro-6H-pyrrolo[1,2-a]pyrimidine-6-carboxamide.

The term "OAB wet" as used herein means overactive bladder as defined by urinary frequency and urinary urgency, with incontinence.

The term "OAB dry" as used herein means overactive bladder as defined by urinary frequency and urinary urgency, without incontinence.

The term "pharmaceutically acceptable salt" means those salts of compounds that are safe and effective for use in subjects and that possess the desired biological activity.

Pharmaceutically acceptable salts of a basic compound can be salts of organic or inorganic acids. In some embodiments, the organic and inorganic acids include but are not limited to hydrochloric acid, hydrobromic acid, sulfuric acid, phosphoric acid, citric acid, maleic acid, mandelic acid, succinic acid and methanesulfonic acid. See generally, *Journal of Pharmaceutical Science*, 66, 2 (1977), which is incorporated herein by reference in its entirety.

The term "$C_{max}$" as used herein refers to the maximum plasma concentration of a drug after it is administered.

The term "$T_{max}$" as used herein refers to the time after administration of a drug when the maximum plasma concentration is reached.

The term "AUC" as used herein refers to the area under the curve of a plot of plasma concentration versus time following administration of a drug.

The term "steady state" means that the amount of the drug reaching the system is approximately the same as the amount of the drug leaving the system. Thus, at "steady-state," the patient's body eliminates the drug at approximately the same rate that the drug becomes available to the patient's system through absorption into the blood stream.

The term "treatment period" means the period of time during which the drug is administered to a subject. For example, the treatment period can be from about 2 weeks to about 2 years. In some embodiments, the treatment period can be about 2, about 4, about 6, about 8, about 10, about 12, about 14, about 16, about 18, about 20, about 24, about 52, about 76 or about 104 weeks. The efficacy of the drug can be assessed by measuring certain parameters and calculating the changes from baseline over the treatment period. The efficacy parameters includes, but are not limited to, micturitions, urge urinary incontinence episodes, total incontinence episodes, and urgency episodes.

Methods of Treatment

The present disclosure relates to a method of treating overactive bladder comprising orally administering to a subject in need thereof a dosage of vibegron such that the desired efficacy is maintained while the undesirable side effects are minimized. It is unexpected that side effects associated with elevated $C_{max}$ can be disproportionally reduced by selection of the dosage of vibegron.

The present disclosure provides a method of treating overactive bladder, the method comprising orally administering to a subject in need thereof an amount of from 50 mg to 100 mg of vibegron per day.

The present disclosure also provides a method of increasing bladder smooth muscle relaxation, the method comprising orally administering to a subject in need thereof an amount of from about 50 mg to about 100 mg of vibegron per day.

In some embodiments, the amount of vibegron administered per day is from about 55 mg to about 100 mg, from about 60 mg to about 100 mg, from about 65 mg to about 100 mg, from about 70 mg to about 100 mg, from about 75 mg to about 100 mg, from about 80 mg to about 100 mg, from about 85 mg to about 100 mg, from about 90 mg to about 100 mg, or from about 95 mg to about 100 mg.

In some embodiments, the amount of vibegron administered per day is from about 50 mg to about 95 mg, from about 50 mg to about 90 mg, from about 50 mg to about 85 mg, from about 50 mg to about 80 mg, from about 50 mg to about 75 mg, from about 50 mg to about 70 mg, from about 50 mg to about 65 mg, from about 50 mg to about 60 mg, or from about 50 mg to about 55 mg.

In some embodiments, the amount of vibegron administered per day is from about 60 mg to about 90 mg, from about 65 mg to about 85 mg, or from about 70 mg to about 80 mg. In some embodiments, the amount of vibegron administered per day is from 60 mg to 90 mg, from 65 mg to 85 mg, or from 70 mg to 80 mg.

In some embodiments, the amount of vibegron administered per day is about 55 mg, about 60 mg, about 65 mg, about 70 mg, about 75 mg, about 80 mg, about 85 mg, about 90 mg, or about 95 mg. In some embodiments, the amount of vibegron administered per day is about 75 mg. In some embodiments, the amount of vibegron administered per day is 75 mg.

In some embodiments, the amount of vibegron administered per day is not about 50 mg. In some embodiments, the amount of vibegron administered per day is not about 100 mg. In some embodiments, the amount of vibegron administered per day is not 50 mg. In some embodiments, the amount of vibegron administered per day is not 100 mg.

In some embodiments, the subject has the symptoms of urgency urinary incontinence, urinary urgency, and urinary frequency.

In some embodiments, the subject has one or more symptoms of urgency urinary incontinence (or urge urinary incontinence), urinary urgency, urinary frequency and nocturia.

In some embodiments, the subject is a mammal. In some embodiments the subject is a human or an animal. In some embodiments, the subject is a human.

In some embodiments, the subject is over the age of 18 years. In some embodiments, the subject is under the age of about 18 years. In some embodiments, the subject is between about 6 to about 18 years, about 6 to about 12 years, or about 12 to about 18 years. In some embodiments, the subject is over the age of about 20 years. In some embodiments the subject is over the age of about 25 years. In some embodiments, the subject is over the age of about 30 years. In some embodiments, the subject is over the age of about 35 years. In some embodiments, the subject is over the age of 40 years. In some embodiments, the subject is over the age of 45 years. In some embodiments, the subject is over the age of 50 years. In some embodiments, the subject is over the age of 55 years. In some embodiments, the subject is over the age of 60 years. In some embodiments, the subject is over the age of 65 years. In some embodiments, the subject is over the age of 70 years. In some embodiments, the subject is over the age of 75 years.

In some embodiments, the method comprises crushing a pharmaceutical unit dose composition comprising vibegron before administration to a subject. In some embodiments, the subject is orally administered a crushed pharmaceutical unit dose comprising vibegron.

In some embodiments, the subject suffers from renal impairment or is at risk of suffering from renal impairment. In some embodiments, the subject suffers from mild renal impairment, moderate renal impairment, or severe renal impairment.

In some embodiments, the subject has received prior OAB therapy. In some embodiments, the subject has not received prior OAB therapy.

In some embodiments the subject suffers from renal impairment and is administered about 75 mg of vibegron per day.

In some embodiments, vibegron is administered with a second pharmaceutical agent, including, e.g., any recited in the present application. In some embodiments, vibegron is administered concomitantly with the second pharmaceutical agent. In some embodiments, vibegron is administered sequentially with the second pharmaceutical agent. In some embodiments, vibegron is administered before and/or after the second pharmaceutical agent. The embodiments described below include such sequential administrations In some embodiments, the subject is concomitantly receiving, taking or otherwise being exposed to a cytochrome P450 inhibitor, such as a CYP3A inhibitor, and with drugs that are substrates of the following CYPs: CYP1A2, 2B6, 2C8, 2C9, 2C19, 2D6, and 3A4.

In some embodiments, the subject is concomitantly receiving, taking, or otherwise being exposed to a P-glycoprotein inhibitor.

CYP3A/P-glycoprotein inhibitors include but are not limited to amiodarone, carvedilol, clarithromycin, dronedarone, itraconazole, lapatinib, lopinavir and ritonavir, propafenone, quinidine, ranolazine, ritonavir, saquinavir and ritonavir, telaprevir, tipranavir and ritonavir, verapamil, curcumin, cyclosporine A, eltrombopag, atazanavir and ritonavir, clarithromycin, cyclosporine, erythromycin, gemfibrozil, lopinavir and ritonavir, rifampin (e.g., single dose), simeprevir, p-aminohippuric acid (PAH)(b), probenecid, teriflunomide, cimetidine, dolutegravir, isavuconazole, ranolazine, trimethoprim, and vandetanib.

In some embodiments, the subject is concomitantly receiving, taking or otherwise being exposed to a muscarinic receptor antagonist Muscarinic receptor antagonists include but are not limited to scopolamine, atropine, hydroxyzine, ipratropium, tropicamide, pirenzepine, diphenhydramine, doxylamine, dimenhydrinate, dicyclomine, flavoxate, oxybutynin, tiotropium, cyclopentolate, atropine methonitrate, trihexyphenidyl/benzhexol, tolterodine, solifenacin, darifenacin, benztropine, Mebeverine, procyclidine, and aclidinium bromide.

In some embodiments, the subject is administered about 75 mg of vibegron per day and is concomitantly receiving, taking or otherwise being exposed to a muscarinic receptor antagonist.

In some embodiments, the subject is administered about 75 mg of vibegron per day and is concomitantly receiving, taking or otherwise being exposed to a CYP3A inhibitor.

In some embodiments, the subject is administered about 75 mg of vibegron per day and is concomitantly receiving, taking, or otherwise being exposed to a P-glycoprotein inhibitor.

In some embodiments the subject is not concomitantly receiving, taking, or otherwise being exposed to a beta blocker.

In some embodiments the subject is not concomitantly receiving, taking, or otherwise being exposed to a amlodipine.

In some embodiments, vibegron is administered with a meal, within 60 minutes after a meal, or within 2 hours after a meal.

In some embodiments, vibegron is administered without a meal or before a meal. In some embodiments, vibegron is administered more than two hours before a meal. In some embodiments vibegron is administered regardless of whether the subject has or has not had a meal.

In some embodiments, vibegron is administered once per day, twice per day, or three times per day. In some embodiments, vibegron is administered once per day.

Changes from baseline in blood pressure (BP) and heart rate (HR) for the subjects taking vibegron are not substantially different for the subjects taking a placebo. In some embodiments, the subject experiences a mean maximum change of systolic blood pressure (SBP) from baseline over the treatment period (e.g., 8 weeks or 12 weeks), and the mean maximum change is less than 2.0 mm/Hg, less than 1.9 mm/Hg, less than 1.8 mm/Hg, less than 1.7 mm/Hg, less than 1.6 mm/Hg, less than 1.5 mm/Hg, less than 1.4 mm/Hg, less than 1.3 mm/Hg, less than 1.2 mm/Hg, less than 1.1 mm/Hg, less than 1.0 mm/Hg, less than 0.9 mm/Hg, less than 0.8 mm/Hg, less than 0.7 mm/Hg, less than 0.6 mm/Hg, or less than 0.5 mm/Hg from that of a subject taking a placebo.

In some embodiments, the subject is administered about 75 mg of vibegron per day, and experiences a mean maximum change of SBP from baseline over the treatment period (e.g., 8 weeks or 12 weeks) of less than 2 mm/Hg from that of a subject taking a placebo. In some embodiments, the subject is administered about 75 mg of vibegron per day, and experiences a mean maximum change of SBP from baseline over the treatment period (e.g., 8 weeks or 12 weeks) of less than 1 mm/Hg from that of a subject taking a placebo.

In some embodiments, the subject is over the age of 65 and is administered about 75 mg of vibegron per day, and experiences a mean maximum change of SBP from baseline over the treatment period (e.g., 8 weeks or 12 weeks) of less than 2 mm/Hg from that of a subject taking a placebo. In some embodiments, the subject is over the age of 65 and is administered about 75 mg of vibegron per day, and experiences a mean maximum change of SBP from baseline over the treatment period (e.g., 8 weeks or 12 weeks) of less than 1 mm/Hg from that of a subject taking a placebo.

In some embodiments, the subject is over the age of 45 and is administered about 75 mg of vibegron per day, and experiences a mean maximum change of SBP from baseline over the treatment period (e.g., 8 weeks or 12 weeks) of less than 2 mm/Hg from that of a subject taking a placebo. In some embodiments, the subject is over the age of 45 and is administered about 75 mg of vibegron per day, and experiences a mean maximum change of SBP from baseline over the treatment period (e.g., 8 weeks or 12 weeks) of less than 1 mm/Hg from that of a subject taking a placebo.

In some embodiments, the subject experiences a mean maximum change of diastolic blood pressure (DBP) from baseline over the treatment period (e.g., 8 weeks or 12 weeks), and the mean maximum change is less than 2.0 mm/Hg, less than 1.9 mm/Hg, less than 1.8 mm/Hg, less than 1.7 mm/Hg, less than 1.6 mm/Hg, less than 1.5 mm/Hg, less than 1.4 mm/Hg, less than 1.3 mm/Hg, less than 1.2 mm/Hg, less than 1.1 mm/Hg, less than 1.0 mm/Hg, less than 0.9 mm/Hg, less than 0.8 mm/Hg, less than 0.7 mm/Hg, less than 0.6 mm/Hg, or less than 0.5 mm/Hg from that of a subject taking a placebo.

In some embodiments, the subject is administered about 75 mg of vibegron per day, and experiences a mean maximum change of DBP from baseline over the treatment period (e.g., 8 weeks or 12 weeks) of less than 2 mm/Hg from that of a subject taking a placebo. In some embodiments, the subject is administered about 75 mg of vibegron per day, and experiences a mean maximum change of DBP from baseline over the treatment period (e.g., 8 weeks or 12 weeks) of less than 1 mm/Hg from that of a subject taking a placebo.

In some embodiments, the subject is over the age of 65 and is administered about 75 mg of vibegron per day, and experiences a mean maximum change of DBP from baseline over the treatment period (e.g., 8 weeks or 12 weeks) of less than 2 mm/Hg from that of a subject taking a placebo. In some embodiments, the subject is over the age of 65 and is administered about 75 mg of vibegron per day, and experiences a mean maximum change of DBP from baseline over the treatment period (e.g., 8 weeks or 12 weeks) of less than 1 mm/Hg from that of a subject taking a placebo.

In some embodiments, the subject is over the age of 45 and is administered about 75 mg of vibegron per day, and experiences a mean maximum change of DBP from baseline over the treatment period (e.g., 8 weeks or 12 weeks) of less than 2 mm/Hg from that of a subject taking a placebo. In some embodiments, the subject is over the age of 45 and is administered about 75 mg of vibegron per day, and experiences a mean maximum change of DBP from baseline over the treatment period (e.g., 8 weeks or 12 weeks) of less than 1 mm/Hg from that of a subject taking a placebo.

In some embodiments, the subject is over the age of 45, is administered about 75 mg of vibegron once per day, and experiences a mean maximum change of DBP from baseline over the treatment period (e.g., 8 weeks or 12 weeks) of less than 1 mm/Hg from that of a subject taking a placebo, and a mean maximum change of SBP from baseline over the treatment period (e.g., 8 weeks or 12 weeks) of less than 1 mm/Hg from that of a subject taking a placebo.

In some embodiments, the subject is over the age of 65, is administered about 75 mg of vibegron once per day, and experiences a mean maximum change of DBP from baseline over the treatment period (e.g., 8 weeks or 12 weeks) of less than 1 mm/Hg from that of a subject taking a placebo, and a mean maximum change of SBP from baseline over the treatment period (e.g., 8 weeks or 12 weeks) of less than 1 mm/Hg from that of a subject taking a placebo.

In some embodiments, the subject experiences a mean maximum change of systolic blood pressure (SBP) from baseline over the treatment period (e.g., 8 weeks or 12 weeks) of less than 10 mm/Hg, less than 9.5 mm/Hg, less than 9 mm/Hg, less than 8.5 mm/Hg, less than 8 mm/Hg, less than 7.5 mm/Hg, less than 7 mm/Hg, less than 6.5 mm/Hg, less than 6 mm/Hg, less than 5.5 mm/Hg, or less than 5 mm/Hg.

In some embodiments, the subject is administered about 75 mg of vibegron per day, and experiences a mean maximum change of SBP from baseline over the treatment period (e.g., 8 weeks or 12 weeks) of less than 10 mm/Hg.

In some embodiments, the subject is over the age of 65 and is administered about 75 mg of vibegron per day, and experiences a mean maximum change of SBP from baseline over the treatment period (e.g., 8 weeks or 12 weeks) of less than 10 mm/Hg.

In some embodiments, the subject is over the age of 45 and is administered about 75 mg of vibegron per day, and experiences a mean maximum change of SBP from baseline over the treatment period (e.g., 8 weeks or 12 weeks) of less than 10 mm/Hg.

In some embodiments, the subject experiences a mean maximum change of diastolic blood pressure (DBP) from baseline over the treatment period (e.g., 8 weeks or 12 weeks) of less than 7 mm/Hg, less than 6.5 mm/Hg, less than 6 mm/Hg, less than 5.5 mm/Hg, less than 5 mm/Hg, less than 4.5 mm/Hg, less than 4 mm/Hg, less than 3.5 mm/Hg, less than 3 mm/Hg, less than 2.5 mm/Hg, or less than 2 mm/Hg.

In some embodiments, the subject is administered about 75 mg of vibegron per day, and experiences a mean maximum change of DBP from baseline over the treatment period (e.g., 8 weeks or 12 weeks) of less than 7 mm/Hg.

In some embodiments, the subject is administered about 75 mg of vibegron per day, and experiences a change from baseline over the treatment period (e.g., 8 weeks or 12 weeks) in average number of micturitions per 24 hours, wherein the change is greater than that for a subject taking placebo. The difference from placebo is from about −0.4 to about −1.5, for example, about −0.4, −0.5, −0.6, −0.7, −0.8, −0.9, −1.0, −1.1, −1.2, −1.3, −1.4, or −1.5, or a range between any two of the preceding values.

In some embodiments, the subject is administered about 75 mg of vibegron per day, and experiences a change from baseline over the treatment period (e.g., 8 weeks or 12 weeks) in average number of micturitions per 24 hours of from about −1.5 to about −2.5, for example, about −1.5, −1.6, −1.7, −1.8, −1.9, −2.0, −2.1, −2.2, −2.3, −2.4, or −2.5, or a range between any two of the preceding values.

In some embodiments, the subject has an average of ≥1 urge urinary incontinence (UUI) episodes per day prior to treatment and is administered about 75 mg of vibegron per day, and experiences a change from baseline over the treatment period (e.g., 8 weeks or 12 weeks) in average number of UUI episodes, wherein the change is greater than that for a subject taking placebo. The difference from placebo is from about −0.2 to about −1.5, for example, about −0.2, −0.3, −0.4, −0.5, −0.6, −0.7, −0.8, −0.9, −1.0, −1.1, −1.2, −1.3, −1.4, or −1.5, or a range between any two of the preceding values.

In some embodiments, the subject is administered about 75 mg of vibegron per day, and experiences a change from baseline over the treatment period (e.g., 8 weeks or 12 weeks) in average number of UUI episodes of from about −1.3 to about −2.5, for example, about −1.3, −1.4, −1.5, −1.6, −1.7, −1.8, −1.9, −2.0, −2.1, −2.2, −2.3, −2.4, or −2.5, or a range between any two of the preceding values.

In some embodiments, the subject is administered about 75 mg of vibegron per day, and experiences a change in the volume voided (mL) per micturition, wherein the change is greater than that for a subject taking placebo. The difference from placebo is from about 20 mL to about 35 mL, for example, about 20 mL, 21 mL, 22 mL, 23 mL, 24 mL, 25 mL, 26 mL, 27 mL, 28 mL, 29 mL, 30 mL, 31 mL, 32 mL, 33 mL, 34 mL, or 30 mL, or a range between any two of the preceding values.

In some embodiments, the subject has an average of ≥1 urge urinary incontinence (UUI) episodes per day prior to treatment and is administered about 75 mg of vibegron per day, and experiences at least 50%, at least 55%, at least 60%, at least 65%, at least 70%, at least 75%, at least 80%, or at least 85% reduction in the average number of daily UUI episodes over the treatment period (e.g., 8 weeks or 12 weeks).

In some embodiments, the subject has an average of ≥1 urgency episodes per day prior to treatment and is administered about 75 mg of vibegron per day, and experiences at least 30%, at least 40%, at least 45%, at least 50%, at least 55%, at least 60%, at least 65%, at least 70%, or at least 75% reduction in the average number of daily urgency episodes over the treatment period (e.g., 8 weeks or 12 weeks).

In some embodiments, the subject is over the age of 65 and is administered about 75 mg of vibegron per day, and experiences a mean maximum change of DBP from baseline over the treatment period (e.g., 8 weeks or 12 weeks) of less than 7 mm/Hg.

In some embodiments, the subject is over the age of 45 and is administered about 75 mg of vibegron per day, and experiences a mean maximum change of DBP from baseline over the treatment period (e.g., 8 weeks or 12 weeks) of less than 7 mm/Hg.

In some embodiments, the subject over the age of 45 is administered about 75 mg of vibegron once per day, experiences a mean maximum change of DBP from baseline over the treatment period (e.g., 8 weeks or 12 weeks) of less than 7 mm/Hg, and a mean maximum change of SBP from baseline over the treatment period (e.g., 8 weeks or 12 weeks) of less than 10 mm/Hg.

In some embodiments, the subject over the age of 65 is administered about 75 mg of vibegron once per day, experiences a mean maximum change of DBP from baseline over the treatment period (e.g., 8 weeks or 12 weeks) of less than 7 mm/Hg, and a mean maximum change of SBP from baseline over the treatment period (e.g., 8 weeks or 12 weeks) of less than 10 mm/Hg.

In some embodiments, vibegron has onset of action of about 4 weeks. In some embodiments, vibegron has onset of action of about 3 weeks. In some embodiments, vibegron has onset of action of about 2 weeks. "Onset of action," as used herein, refers to the duration of time it takes for a drug's effects to come to prominence upon administration.

Pharmaceutical Unit Dose Composition

The present disclosure provides pharmaceutical unit dose compositions comprising a dosage of vibegron disclosed herein, wherein the unit dosage composition is suitable for oral administration. Oral dosage forms are recognized by those skilled in the art to include, for example, such forms as liquid formulations, tablets, capsules, and gelcaps. In some embodiments, the unit dose compositions are solid dosage forms, such as tablets and capsules. In some embodiments, the unit dose compositions are tablets.

Pharmaceutically acceptable excipients are excipients generally recognized as safe such as lactose, microcrystalline cellulose, starch, calcium carbonate, magnesium stearate, stearic acid, talc, colloidal silicon dioxide, mannitol, croscarmellose sodium, hydroxypropyl cellulose. In some embodiments, the pharmaceutical unit dose composition disclosed herein comprises a diluent, a disintegrant, a binder, and a lubricant. See generally, Remington's Pharmaceutical Sciences, 20th ed., Mack Publishing, Easton PA (2000), which is incorporated herein by reference in its entirety.

In one embodiment, the pharmaceutical unit dose composition disclosed herein comprises mannitol, microcrystalline cellulose, croscarmellose sodium, hydroxypropyl cellulose, and magnesium stearate.

Oral dosage forms can be prepared by standard pharmaceutical manufacturing techniques. Such techniques include, for example, wet granulation, wet milling, fluid bed drying, dry milling, lubrication, tableting, and aqueous film coating.

In some embodiments, the pharmaceutical unit dose compositions of the present disclosure comprise from about 50 mg to about 100 mg of vibegron.

In some embodiments, the pharmaceutical unit dose compositions of the present disclosure comprise from about 55 mg to about 100 mg, from about 60 mg to about 100 mg, from about 65 mg to about 100 mg, from about 70 mg to about 100 mg, from about 75 mg to about 100 mg, from about 80 mg to about 100 mg, from about 85 mg to about 100 mg, from about 90 mg to about 100 mg, or from about 95 mg to about 100 mg of vibegron.

In some embodiments, the pharmaceutical unit dose compositions of the present disclosure comprise from about 50 mg to about 95 mg, from about 50 mg to about 90 mg, from about 50 mg to about 85 mg, from about 50 mg to about 80 mg, from about 50 mg to about 75 mg, from about 50 mg to about 70 mg, from about 50 mg to about 65 mg, from about 50 mg to about 60 mg, or from about 50 mg to about 55 mg of vibegron.

In some embodiments, the pharmaceutical unit dose compositions of the present disclosure comprise from about 60 mg to about 90 mg, from about 65 mg to about 85 mg, or from about 70 mg to about 80 mg of vibegron. In some embodiments, the pharmaceutical unit dose compositions of the present disclosure comprise from 60 mg to 90 mg, from 65 mg to 85 mg, or from 70 mg to 80 mg of vibegron.

In some embodiments, the pharmaceutical unit dose compositions of the present disclosure comprise about 55 mg, about 60 mg, about 65 mg, about 70 mg, about 75 mg, about 80 mg, about 85 mg, about 90 mg, or about 95 mg of vibegron. In some embodiments, the pharmaceutical unit dose compositions of the present disclosure comprise about 75 mg of vibegron. In some embodiments, the pharmaceutical unit dose compositions of the present disclosure comprise 75 mg of vibegron.

In some embodiments, the pharmaceutical unit dose compositions of the present disclosure can be crushed. In some embodiments, the pharmaceutical unit dose compositions of the present disclosure are crushed before oral administration.

In-Vitro Assays

Vibegron was tested in several in vitro assays to determine its agonist potency at human $\beta_3$-AR, its selectivity versus the other human $\beta$-AR subtypes, and its potency at $\beta_3$-ARs from other species.

Vibegron activity was measured in a functional assay measuring increases in cellular adenylyl cyclase activity in Chinese hamster ovary (CHO) cells stably expressing the human $\beta_3$-AR. The degree of activation relative to a proven full agonist (isoproterenol) was measured along with the compound $EC_{50}$.

Vibegron is a potent and selective agonist of $\beta_3$-AR, with an $EC_{50}$ of 1.1 nM and 84% activation relative to isoproterenol. A small serum shift is observed in the presence of 40% human serum ($EC_{50}$=1.7 nM, 102% activation), consistent with the low plasma protein binding (49% unbound in human) of this compound.

In addition, the selectivity of vibegron for $\beta_3$-AR over $P_1$- and $\beta_2$-AR subtypes was determined by testing in CHO cells expressing either $\beta_1$-AR or $\beta_2$-AR. Vibegron is highly selective over $\beta_1$-AR and $\beta_2$-AR versus $\beta_3$-AR, demonstrating >9000-fold selectivity for activation of $\beta_3$-AR over $\beta_1$-AR or $\beta_2$-AR in cell based in vitro functional assays.

The $IC_{50}$ of vibegron was determined in a standard competition binding assay using membranes prepared from cells expressing recombinant $P_1$, $\beta_2$ or $\beta_3$-AR. Vibegron has a $\beta_3$-AR $IC_{50}$=193 nM (86 ng/mL) for competition of a non-specific $\beta$-AR radiolabeled antagonist $^{125}$I-CYP in a filter binding assay. The relative lack of binding affinity compared to the potent in vitro agonist activity of vibegron at the human $\beta_3$-AR is related to the relative ability of the compound to compete for uncoupled versus coupled receptors which would both be measured by the antagonist binding assay. In addition, the compound does not bind to either $\beta_1$-AR or $\beta_2$-AR as demonstrated in binding competition assays, confirming that the compound is neither an agonist nor an antagonist at these receptors.

Absorption, Distribution, Metabolism, and Excretion

Vibegron reaches maximum plasma concentrations ($C_{max}$) at approximately 1 to 3 hours after oral administration in healthy volunteers. Mean $C_{max}$ and AUC increase in a greater than dose-proportional manner up to 400 mg. Steady state concentrations were achieved within 7 days of once daily dosing of vibegron. The steady state AUC geometric mean accumulation ratios were ~2 in young male subjects and ~2.8 in elderly subjects (male and female). Vibegron exposures in young Japanese male subjects were modestly increased (<2-fold) following single-dose administration relative to exposures in non-Japanese young male subjects.

Administration of multiple oral doses of 150 mg vibegron with food in healthy middle-aged and elderly females resulted in mean $AUC_{0-24}$ and $C_{max}$ values of ~42% and 59% on Day 1 and ~20% and 43% on Day 14 compared to the same dose in the fasted state.

In a two-part, open-label, single-dose study to investigate the pharmacokinetics of vibegron in patients with hepatic insufficiency the apparent volume of distribution (Vd/F) for vibegron was approximately 9120 L. Vibegron is bound (approximately 49%) to human plasma proteins.

Vibegron is eliminated by a variety of pathways including urinary excretion, biliary excretion, and hepatic metabolism. While CYP3A4 is the predominant CYP responsible for in vitro metabolism, metabolism appears to only play a minor role in the elimination of vibegron. In a mass balance study in healthy subjects, the majority of the recovered dose was eliminated as unchanged vibegron. The mean total recovery of radioactivity in the excreta was 79%, with approximately 59% and 20% of the dose recovered in feces and urine, respectively.

Figure 2:
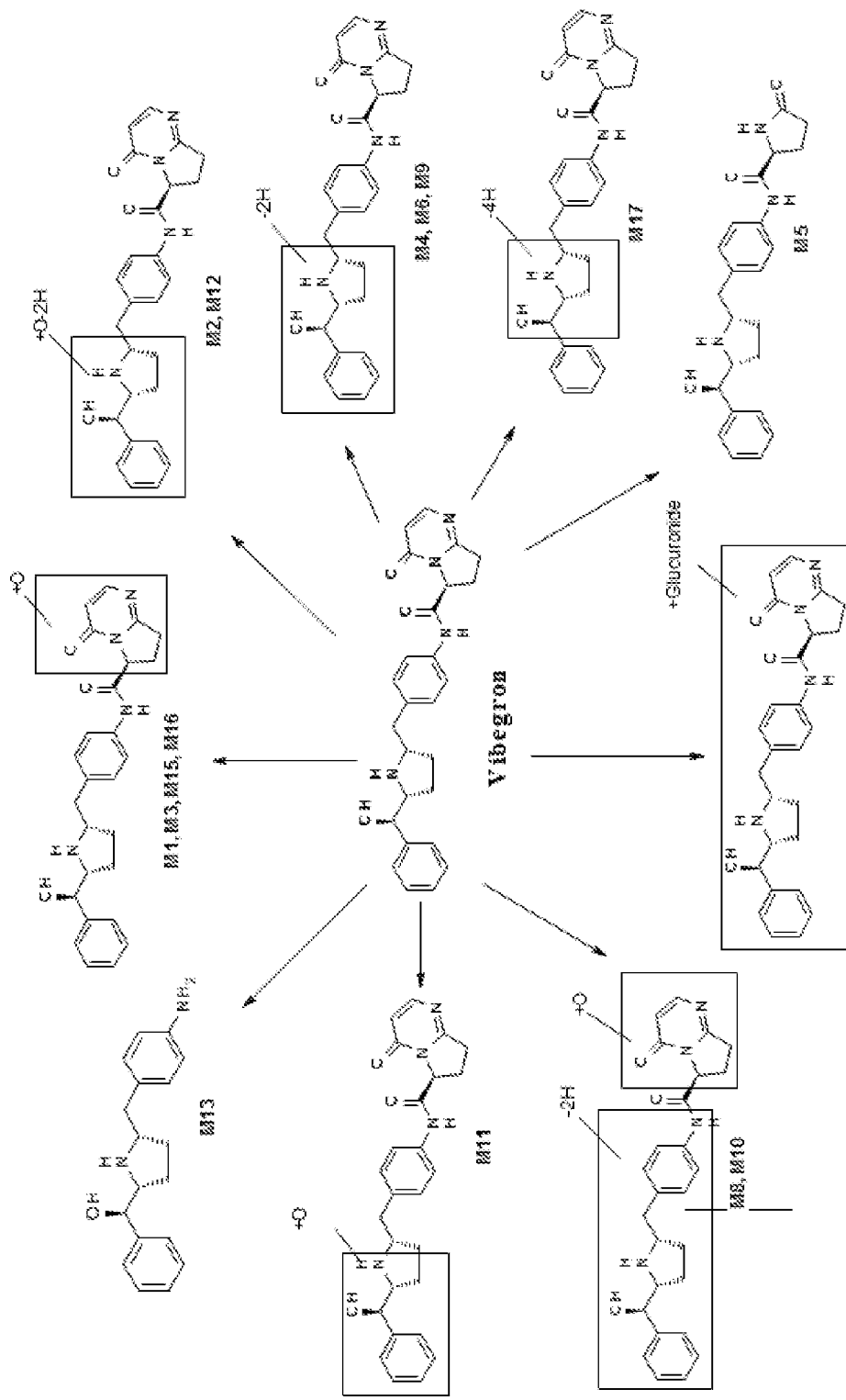
FIG. 2 depicts the chemical structures of vibegron's metabolites.

It was found that most of the vibegron dose was eliminated as the unchanged parent drug. Seven minor metabolites were detected in urine and feces, six of which (M1, M3, M4, M6, M11, and M17) were oxidative metabolites (see FIG. 2). The metabolite M7 is an O-glucuronide conjugate of vibegron. The concentration of [$^{14}$C]vibegron derived radioactivity in plasma had an average $C_{max}$ of 0.3 μM and a $T_{max}$ of 2.5 hr. The radioactive profiles of plasma samples at 2 and 4 hr indicated that ~78% and ~73% of the plasma radioactivity, respectively, was accounted for by the unchanged vibegron, and the 0-glucuronide (M7) was the predominant circulating metabolite (~12-14% of the total circulating drug-related material). Two additional minor oxidative metabolites M4 (4-6%) and M17 (6-7%) were also detected in human plasma. The radioactivity in plasma samples at other time points beyond 4 h post dosing was too low to be profiled. The accumulation potential of circulating metabolites in plasma was not estimated due to insufficient data from later time points to enable estimation of half-life.

Vibegron has a terminal $t_{1/2}$ of 59-94 hours in young and elderly subjects. At steady state, the average renal clearance (CLR) in young males ranged from 150 to 187 mL/min across all dose levels, while CLR in elderly subjects (male and female) was slightly less at 127 mL/min. There was a trend of increasing fraction of the dose excreted at steady state ($fe_{0-24hr}$, ss) with increasing dose, reflecting the increase in bioavailability as the dose increased. The $fe_{0-24hr}$, ss was similar in young males and elderly, ~14% at 100 and 150 mg in young males and ~17% at 100 mg in elderly subjects. The mean $fe_{0-24hr}$ and $CL_R$ in young Japanese subjects were similar to what was observed in non-Japanese subjects.

EXAMPLES

Example 1

Vibegron Tablet Formulation

The composition of vibegron tablets (50 mg, 75 mg, and 100 mg) is shown in Table 1.

TABLE 1

Vibegron Tablet Compositions

| Components | Function | Unit Strength | | |
|---|---|---|---|---|
| | | 50 mg mg/tablet | 75 mg mg/tablet | 100 mg mg/tablet |
| Core Tablet | | | | |
| MK4618 | Active | 50.00 | 75.00 | 100.0 |
| Mannitol | Diluent | 20.75 | 31.125 | 41.50 |
| Microcrystalline Cellulose | Diluent | 20.75 | 31.125 | 41.50 |
| Croscarmellose Sodium | Disintegrant | 3.000 | 4.500 | 6.000 |
| Hydroxypropyl Cellulose | Binder | 4.500 | 6.75 | 9.000 |

TABLE 1-continued

Vibegron Tablet Compositions

| | | Unit Strength | | |
|---|---|---|---|---|
| Components | Function | 50 mg mg/tablet | 75 mg mg/tablet | 100 mg mg/tablet |
| Magnesium Stearate | Lubricant | 1.000 | 1.500 | 2.000 |
| Purified Water[1] | Solvent | (35.00-45.00) | (52.5-67.5) | (70.00-90.00) |
| Total Core Weight | | 100.0 | 150.0 | 200.00 |
| Film Coating Suspension | | | | |
| Purified Water[1] | Solvent | (45.00) | (67.50 | (90.00) |
| OPADRY II Green (39K110004) | Colorant | 5.000 | 7.500 | 10.00 |
| Total | | 105.0 | 157.5 | 210.0 |

[1]Removed during processing

Example 2

Pharmacokinetic Data

2.1 Single-Dose Pharmacokinetics

Single-dose pharmacokinetics of vibegron were examined in two double-blind, randomized, placebo-controlled, single rising oral dose Phase 1 studies. All subjects were healthy adults. A summary of the results is presented in Table 2. Following single oral vibegron doses ranging from 2 to 600 mg, the average $t_{max}$ occurred between 0.8 and 3 hours after dosing. Terminal elimination $t_{1/2}$ averaged 43 to 75 hours for all doses from 10 to 600 mg in healthy young male subjects. Systemic exposures were greater than dose proportional up to 600 mg.

Vibegron exposures in Japanese young males were modestly increased relative to exposures in non-Japanese young males. Geometric mean ratios (GMRs; Japanese/non-Japanese) for vibegron $AUC_{0-inf}$ and corresponding 90% CIs decreased with increasing dose, from 1.75 (1.38, 2.23) at 10 mg to 1.17 (0.99, 1.40) at 300 mg. The GMR (Japanese/non-Japanese) and 90% CI for vibegron $C_{max}$ did not appear to be influenced by dose and was 1.75 (1.35, 2.26) pooled across all doses. Median $T_{max}$ values (1 to 3 hours) and harmonic mean apparent terminal $t_{1/2}$ estimates (58 to 71 hours) in the Japanese subjects were similar to those in the non-Japanese subjects. Similar to non-Japanese subjects, $AUC_{0-inf}$ and $C_{max}$ in the Japanese subjects appeared to increase in a greater than dose proportional manner up to 300 mg.

Single-dose pharmacokinetics of 50 mg vibegron in non-Japanese elderly male and female subjects are also presented in Table 2. In elderly male and female subjects, mean $AUC_{0-inf}$ and $C_{max}$ following administration of 50 mg vibegron were ~70% and 60% higher, respectively, relative to corresponding values following 50 mg in young males. $T_{max}$ was similar to that observed in young males (median $T_{max}$=1.0 hr), while the apparent terminal $t_{1/2}$ was slightly longer in elderly relative to young (harmonic mean $t_{1/2}$=92 vs. 52 hr). Vibegron exposures in elderly females were somewhat higher than in elderly males.

TABLE 2

Summary of Selected Single Dose Plasma Vibegron Pharmacokinetic Parameters

| Dose (mg)[a] | N | $AUC_{0-inf}$ (ng · h/mL) | $AUC_{0-24}$ (ng · h/mL) | $C_{max}$ (ng/mL) | $T_{max}$[b] (hr) | $t_{1/2}$[c] (hr) |
|---|---|---|---|---|---|---|
| 2 | 3[d] | —[e] | 0.80 ± 0.33 | 0.28 ± 0.02 | 3.0 (1.0-3.0)[c] | —[e] |
| 5 | 6 | —[e] | 8.31 ± 4.80 | 0.79 ± 0.30 | 1.0 (0.5-6.0) | —[e] |
| 10 | 6 | 70.7 ± 34.9 | 30.0 ± 12.6 | 4.76 ± 4.58 | 2.5 (1.0-6.0) | 43.2 ± 13.0 |
| 10 (Japanese) | 6 | 98.7 ± 27.3 | 31.0 ± 9.33 | 3.34 ± 1.97 | 1.0 (1.0-4.0) | 57.6 ± 39.0 |
| 20 | 6 | 121 ± 48.9 | 40.0 ± 21.1 | 5.25 ± 4.25 | 0.8 (0.5-6.0) | 64.2 ± 12.6 |
| 50 | 6 | 551 ± 262 | 219 ± 123 | 31.7 ± 35.0 | 2.0 (0.5-6.0) | 52.0 ± 7.8 |
| 50 (Japanese) | 6 | 885 ± 241 | 385 ± 136 | 62.2 ± 20.4 | 3.0 (0.5-3.0) | 64.4 ± 8.7 |
| 50 (Elderly Male and Female) | 12 | 951 ± 300 | 314 ± 119 | 50.2 ± 23.6 | 1.0 (0.5-3.0) | 92.1 ± 15.9 |
| 100 | 6 | 1890 ± 698 | 845 ± 401 | 142 ± 108 | 2.0 (1.0-4.0) | 72.8 ± 10.8 |
| 100 (Japanese) | 6 | 1770 ± 418 | 920 ± 300 | 190 ± 123 | 2.5 (0.5-4.0) | 57.6 ± 12.0 |
| 150 | 6 | 2270 ± 911 | 1050 ± 551 | 195 ± 185 | 1.0 (1.0-6.0) | 60.5 ± 10.5 |
| 200 | 18 | 3630 ± 1110 | 1740 ± 748 | 274 ± 138 | 1.0 (1.0-4.0) | 75.3 ± 9.1 |
| 200 (Japanese) | 6 | 5200 ± 791 | 3090 ± 569 | 516 ± 200 | 2.0 (0.5-4.0) | 58.4 ± 9.0 |
| 300 | 6 | 7380 ± 1410 | 4427 ± 996 | 618 ± 231 | 2.5 (2.0-3.0) | 63.4 ± 3.0 |
| 300 (Japanese) | 6 | 6270 ± 1570 | 4050 ± 1240 | 733 ± 210 | 2.0 (1.0-4.0) | 59.7 ± 9.2 |

TABLE 2-continued

Summary of Selected Single Dose Plasma Vibegron Pharmacokinetic Parameters

| Dose (mg)[a] | N | AUC$_{0-inf}$ (ng · h/mL) | AUC$_{0-24}$ (ng · h/mL) | C$_{max}$ (ng/mL) | T$_{max}$[b] (hr) | t$_{1/2}$[c] (hr) |
|---|---|---|---|---|---|---|
| 450 | 6 | 9157 ± 1850 | 5510 ± 1440 | 645 ± 165 | 3.0 (0.5-6.0) | 60.0 ± 9.4 |
| 600 | 5 | 15500 ± 3450 | 10900 ± 2770 | 1330 ± 529 | 3.0 (2.0-6.0) | 60.5 ± 5.2 |

Concentration data converted from molar to ng/mL (molecular weight of vibegron = 444.5)
[a]Dosed in healthy young males unless otherwise indicated
[b]Median (minimum-maximum)
[c]Harmonic mean ± Pseudo SD
[d]Only 3 of 6 subjects had any concentrations above the limit of quantitation at the 2 mg dose. Summary statistics for C$_{max}$, T$_{max}$ and AUC$_{0-24}$ are based only on data from these subjects.
[e]The duration of sampling was too short for 2 and 5 mg, precluding an accurate determination of the apparent terminal t$_{1/2}$ and AUC$_{0-inf}$

2.2 Multiple-Dose Pharmacokinetics

The multiple-dose pharmacokinetics of vibegron were examined in healthy non-Japanese young male subjects, middle-aged male and female subjects, and elderly male and female subjects, and in healthy Japanese young male subjects, and elderly male and female subjects in two randomized, double-blind, placebo-controlled, multiple rising dose Phase 1 studies. Non-Japanese subjects received multiple doses ranging from 25 to 400 mg for 7 to 28 days, whereas Japanese subjects received multiple doses of 50 to 200 mg for 14 days. Pharmacokinetic results after 14 days of dosing are summarized in Table 3.

On average, females tend to have 50% higher exposures (AUC) compared with males, regardless of age. Steady state AUC and C$_{max}$ values following QD doses of 100 mg vibegron in elderly subjects were about 1.7-fold and 1.3-fold higher, respectively, compared to young males.

The GM C$_{max}$ and AUC accumulation ratio were 1.78 and 1.84 for Japanese subjects at the 200 mg dose level. On average, steady state exposures in the Japanese young male subjects were ~30% higher than those in the young male non-Japanese subjects; differences in exposure were statistically significant. The GMR (Japanese/non-Japanese) and corresponding 90% CI of vibegron AUC and C$_{max}$ pooled across doses were 1.27 (1.09, 1.48) and 1.33 (1.06, 1.67), respectively.

On average, steady state exposures on Day 14 in elderly male and female Japanese subjects were 35% higher than those in elderly male and female non-Japanese subjects; differences in exposure were statistically significant. Day 14 GMR (Japanese/non-Japanese) and corresponding 90% CI of vibegron AUC$_{0-24}$ and C$_{max}$ for the elderly panel were 1.35 (1.09, 1.68) and 1.82 (1.32, 2.51), respectively.

TABLE 3

Summary of Selected Multiple Dose Plasma Vibegron Pharmacokinetic Parameters

| Dose (mg)[a] | N | AUC$_{0-24}$ (ng · h/mL) | C$_{max}$ (ng/mL) | C$_{trough}$ (ng/mL) | T$_{max}$[b] (hr) | t$_{1/2}$[c] (hr) |
|---|---|---|---|---|---|---|
| 25 | 6 | 164 ± 25.9 | 15.6 ± 6.93 | 5.07 ± 0.711 | 1.0 (0.5-2.0) | 94.0 ± 9.60 |
| 50 | 6 | 507 ± 176 | 41.5 ± 12.3 | 15.2 ± 5.07 | 2.5 (0.5-6.0) | 77.2 ± 8.9 |
| 50 (Japanese) | 5 | 613 ± 296 | 56.9 ± 34.2 | 16.5 ± 6.05 | 3.0 (0.5-3.0) | 69.4 ± 6.6 |
| 100 | 6 | 1280 ± 529 | 169 ± 80.9 | 31.9 ± 11.5 | 1.0 (0.5-4.0) | 79.7 ± 11.5 |
| 100 (Japanese) | 6 | 1710 ± 542 | 180 ± 111 | 41.0 ± 11.0 | 2.0 (2.0-4.0) | 56.8 ± 19.2 |
| 100 (Elderly Male and Female) | 12 | 2230 ± 671 | 224 ± 92.0 | 54.2 ± 15.3 | 1.0 (0.5-6.0) | 88.4 ± 10.7 |
| 100 (Elderly Japanese) | 12 | 2920 ± 693 | 393 ± 165 | 57.3 ± 12.2 | 1.5 (0.5-4.0) | 75.1 ± 3.9 |
| 150 | 6 | 2285 ± 1140 | 305 ± 215 | 54.2 ± 16.6 | 1.5 (0.5-4.0) | 79.2 ± 9.2 |
| 150 (Middle-Aged Male) | 9 | 2170 ± 452 | 293 ± 67.1 | 46.2 ± 8.50 | 1.0 (0.5-3.0) | 72.7 ± 16.1[d] |
| 150 (Middle-Aged Female) | 9 | 3180 ± 925 | 246 ± 139 | 62.7 ± 12.4 | 2.0 (1.0-4.0) | 83.1 ± 17.2 |
| 200 | 6 | 3200 ± 1120 | 313 ± 168 | 61.8 ± 12.4 | 2.0 (1.0-3.0) | 64.7 ± 6.5 |
| 200 (Japanese) | 6 | 4370 ± 618 | 631 ± 154 | 62.2 ± 9.07 | 1.0 (0.5-6.0) | 59.5 ± 1.9 |
| 300 | 18 | 6980 ± 1040 | 733 ± 164 | 128 ± 23.6 | 2.0 (2.0-3.0) | 61.7 ± 7.3 |
| 400 | 6 | 10500 ± 2140 | 1400 ± 257 | 189 ± 54.7 | 1.5 (1.0-3.0) | 58.9 ± 5.9 |

Concentration data converted from molar to ng/mL (molecular weight of vibegron = 444.5)
[a]Dosed in healthy young males unless otherwise indicated
[b]Median (minimum-maximum)
[c]Harmonic mean ± Pseudo SD
[d]t$_{1/2}$ determined after 28 days of dosing

2.3 Bioavailability and Bioequivalence

Five Phase 1 studies were conducted using a capsule formulation of vibegron, while seven Phase 1 studies and one Phase 2b study used a tablet formulation. An open-label, randomized, 2-period, crossover PK study in healthy male subjects age 18 to 45 years compared single-dose pharmacokinetics of the capsule (1×150 mg capsule) and tablet (3×50 mg tablets) formulations of vibegron.

The tablet formulation provided comparable exposures to the capsule formulation as demonstrated in Table 4. $T_{max}$ and the apparent terminal $t_{1/2}$ were also similar between the two formulations.

TABLE 4

A Summary of the Effect of Formulation on the Pharmacokinetics of 150 mg Vibegron in Healthy Male Subjects

| Pharmacokinetic Parameter | Geometric Least Squares Mean (95% CI) | | GMR | 90% CI |
|---|---|---|---|---|
| | Capsule[a] | Tablet[b] | | |
| $AUC_{0-inf}$ (ng · hr/mL) | 2840 (2512, 3220) | 2660 (2350, 3010) | 0.94 | (0.87, 1.00) |
| $C_{max}$ (ng/mL) | 237 (190, 295) | 213 (172, 264) | 0.90 | (0.75, 1.08) |

Concentration data converted from molar to ng/mL (molecular weight of vibegron = 444.5)
GMR = Geometric least-squares mean ratio of tablet to capsule
[a] 1 × 150 mg vibegron capsule
[b] 3 × 50 mg vibegron tablets An open-label, single-dose, randomized, two-period, two-treatment, two-sequence, crossover Phase 1 study evaluated the relative bioequivalence of two types of tablets with slightly different composition: aqueous tablet (test) and non-aqueous tablet (reference).

TABLE 5

A Summary of the Effect of Formulation on the Pharmacokinetics of 50 mg Vibegron in Healthy Male and Female Subjects

| Pharmacokinetic Parameter | Geometric Least Squares Mean (95% CI) | | GMR (%) | 90% CI |
|---|---|---|---|---|
| | Reference Tablet[a] | Test Tablet[b] | | |
| $AUC_{0-inf}$ (ng · hr/mL) | 671 (529, 853) | 671 (547, 827) | 100.2 | (91.6, 109.5.) |
| $C_{max}$ (ng/mL) | 38.0 (27.8, 52.1) | 41.0 (30.0, 56.1) | 107.7 | (87.4, 132.7) |

Concentration data converted from molar to ng/mL (molecular weight of vibegron = 444.5)
GMR = Geometric least-squares mean ratio of Phase 3 tablet to Phase 2 tablet
[a] Non-aqueous tablet (PMF1)
[b] Aqueous (PMFII)

2.4 Effect of Food on Oral Absorption

The effect of food on the single dose pharmacokinetics of vibegron 50 mg was evaluated in healthy non-Japanese and Japanese young males in two randomized, double-blind, placebo-controlled, rising single-dose Phase 1 studies, while the effect of food on multiple dose pharmacokinetics of vibegron 150 mg in middle-aged females was evaluated in a randomized, double-blind, placebo-controlled, multiple rising dose Phase 1 study. A summary of the pharmacokinetic results are listed in Table 6.

Administration of 50 mg vibegron with a high-fat meal in non-Japanese young males resulted in 46% and 67% reductions in $AUC_{0-inf}$ and $C_{max}$, respectively, and a delay in $T_{max}$ of ~1 hour compared to administration in the fasted state. Administration of 50 mg vibegron with a standard Japanese breakfast to Japanese young males resulted in 37% and 52% reductions in $AUC_{0-inf}$ and $C_{max}$, respectively, roughly similar to findings in non-Japanese male subjects administered the same dose with a high fat meal.

Administration of multiple oral doses of 150 mg vibegron with food in healthy middle-aged females resulted in 20% and 47% reductions in mean $AUC_{0-24hr}$ and $C_{max}$, respectively, on Day 14 compared to the same dose in the fasted state. $T_{max}$ at steady state was delayed in the fed state compared to the fasted state (6.0 vs. 2.0 hr).

TABLE 6

Summary of Food Effect on Vibegron Pharmacokinetic Parameters following Single and Multiple Dose Administration in the Fed and Fasted State to Healthy Japanese and Non-Japanese Young Male Subjects, and to Healthy Non-Japanese Middle-Aged Female Subjects

| Single Dose (mg) in Young Males | N | Pharmacokinetic Parameters[a] | | | |
|---|---|---|---|---|---|
| | | $AUC_{0-inf}$ (ng · h/mL) | $AUC_{0-24}$ (ng ·h/mL) | $C_{max}$ (ng/mL) | $T_{max}$[b] (hr) |
| 50 (Non-Japanese, fed) | 6 | 316 ± 127 | 90.7 ± 22.9 | 7.6 ± 2.27 | 3.0 (2.0-6.0) |
| 50 (Non-Japanese, fasted) | 6 | 551 ± 262 | 219 ± 123 | 31.7 ± 35.0 | 2.0 (0.5-6.0) |
| 50 (Japanese, fed) | 6 | 605 ± 222 | 226 ± 112 | 36.2 ± 33.3 | 1.5 (0.5-3.0) |
| 50 (Japanese, fasted) | 5 | 885 ± 241 | 385 ± 136 | 62.2 ± 20.4 | 3.0 (0.5-3.0) |

TABLE 6-continued

Summary of Food Effect on Vibegron Pharmacokinetic Parameters following Single and Multiple Dose Administration in the Fed and Fasted State to Healthy Japanese and Non-Japanese Young Male Subjects, and to Healthy Non-Japanese Middle-Aged Female Subjects

| Multiple Dose (mg) in Non-Japanese Middle-Aged Females | N | Pharmacokinetic Parameters[a,c] | | | |
|---|---|---|---|---|---|
| | | $AUC_{0-24}$ (ng · h/mL) | $C_{max}$ (ng/mL) | $C_{trough}$ (ng/mL) | $T_{max}$[b] (hr) |
| 150 (Fed) | 6 | 2540 ± 334 | 185 ± 32.3 | 65.3 ± 7.87 | 6.0 (3.0-6.0) |
| 150 (Fasted) | 9 | 3180 ± 925 | 346 ± 139 | 62.7 ± 12.4 | 2.0 (1.0-4.0) |

Concentration data converted from molar to ng/mL (molecular weight of vibegron = 444.5)
[a]Geometric mean (CV %)
[b]Median (minimum-maximum)
[c]PK parameters obtained at day 14 of vibegron dosing 2.5 Pharmacokinetics in the Target Disease Population A randomized, double-blind, placebo- and active-controlled, parallel-group two-part Phase 2b study in patients with OAB measured sparse vibegron trough concentrations ($C_{trough}$) only; the mean (±SD) $C_{trough}$ of vibegron 50 mg and 100 mg QD were 27.4 (±18.3) ng/mL and 73.6 (±65.5) ng/mL, respectively. Mean (±SD) $C_{trough}$ of vibegron 50 mg in healthy young men was 15.2 (±5.07) ng/mL. Mean (±SD) $C_{trough}$ values of vibegron 100 mg ranged from 31.9 (±11.5) in healthy young men to 54.2 (±15.3) in healthy elderly.

Example 3

Pharmacokinetics in Special Populations 3.1 Effect of Age

Vibegron exposures were evaluated in young (18 to 45 years), middle-aged (46 to 64 years) and elderly (65 to 85 years) males and females. Although exposures were similar in middle-aged males when compared to young males, plasma concentrations were higher in elderly compared to middle-aged and young subjects. After a single 50 mg dose, vibegron $AUC_{0-inf}$ and $C_{max}$ were 70% and 60% higher, respectively in elderly subjects compared with young subjects. Elimination $t_{1⁄2}$ was longer in the elderly at 92 hours compared to 52 hours in young subjects in a randomized, double-blind, placebo-controlled, rising single-dose study. Steady state vibegron $AUC_{0-24h}$ and $C_{max}$ values were ~1.7-fold and ~1.3-fold greater, respectively, in the elderly compared with young males in a randomized, double-blind, placebo-controlled, multiple rising dose study. Furthermore, the steady state AUC geometric mean accumulation ratios were ~2 in young males and ~2.8 in the elderly. In elderly Japanese, $AUC_{0-24}$ and $C_{max}$ were increased by ~35% and 82%, respectively compared to elderly non-Japanese.

3.2 Effect of Gender

The effect of gender on steady-state vibegron exposures after 100 or 150 mg doses was evaluated in a randomized, double-blind, placebo-controlled, multiple rising dose study. Vibegron plasma concentrations were similar in middle-aged males when compared to young males; however, exposures were slightly higher in middle-aged females compared to middle-aged males (~1.5-fold higher steady state AUC in middle-aged females), which was also observed when comparing exposures in elderly females to those in elderly males.

3.3 Effect of Renal Impairment

The pharmacokinetics of single dose vibegron 100 mg in 24 patients with impaired renal function (8 severe, 8 moderate, and 8 mild) were compared to 8 healthy control subjects in an open-label, single-dose PK study. A summary of the pharmacokinetic parameters and a statistical comparison between patients with varying degrees of renal impairment and their healthy matched subjects are presented in Table 7.

Vibegron $AUC_{0-inf}$ in patients with mild (eGFR≥60 to <90 mL/min/1.73 m$^2$), moderate (eGFR≥30 to <60 mL/min/1.73 m$^2$), and severe (eGFR <30 mL/min/1.73 m$^2$ but not on dialysis) renal impairment were 49%, 106%, and 83% higher, respectively, compared to healthy matched control subjects. Vibegron $C_{max}$ in mild, moderate, and severe renal impairment patients were 96%, 68%, and 42% higher, respectively, compared to healthy matched control subjects. In summary, increasing degree of renal impairment was associated with an increase in vibegron $AUC_{0-inf}$ with no clear trend observed in $C_{max}$. Decreasing renal function was associated with lower clearance. The relationship between clearance and renal function was modeled using linear regression. Based on the slope from the regression, CL/F was found to increase ~0.8% per one mL/min/1.73 m$^2$ increase in eGFR. Based on this linear relationship, the CL/F ratio for mild, moderate, and severe populations relative to healthy subjects was predicted to be 0.81, 0.64, and 0.50, respectively. Corresponding predicted ratios for AUC were 1.24, 1.57, and 2.00. Modeling the relationship between CL/F and creatinine Clearance yielded similar results. Renal clearance (CLR) and the fraction of dose excreted in urine over the 48-hour collection interval (fe[urine]48 hr) decreased with increasing degree of renal impairment. Patients with mild, moderate, and severe renal impairment had reduced CLR by 39%, 65%, and 82%, respectively, compared to healthy matched control subjects. The fe[urine] 48 hr was comparable between mild renal impairment patients (8.5%) and healthy matched controlled subjects (7.9%) and was 5.5% and 2.1% in moderate and severe renal impairment patients, respectively.

TABLE 7

Summary of Vibegron 100 mg Pharmacokinetic Parameters in Patients with Severe, Moderate and Mild Renal Impairment and Healthy Matched Control Subjects

| Pharmacokinetic Parameter | N | Geometric Least Squares Mean (95% CI) | | | |
|---|---|---|---|---|---|
| | | Severe Renal Impairment | Moderate Renal Impairment | Mild Renal Impairment | Healthy Matched Control Subjects |
| $AUC_{0-inf}$ (ng · hr/mL) | 8 | 2820 (2200, 3610) | 3170 (2500, 4030) | 2290 (1800, 2920) | 1540 (1180, 2010) |
| $C_{max}$ (ng/mL) | 8 | 152 (103, 225) | 180 (123-262) | 210 (144, 308) | 107 (70.8, 162) |
| CL/F (L/hr) | 8 | 35.5 (27.68, 45.53) | 31.5 (24.80, 40.06) | 43.6 (34.23, 55.61) | 64.9 (49.87, 84.47) |
| $T_{max}{}^a$ (hr) | 8 | 0.5 (0.5-4.0) | 1.3 (0.5-3.0) | 1.0 (0.5-3.0) | 1.5 (0.5-4.0) |
| Apparent terminal $t_{1/2}{}^b$ (hr) | 8 | 131 (10.0) | 108 (21.0) | 96.2 (11.5) | 98.8 (13.9) |
| $CL_R{}^b$ (L/hr) | 8 | 1.9 (30.9) | 3.6 (34.5) | 6.3 $(31.1)^c$ | 10.4 (20.2) |
| Fe[urine]48 hr $^b$ (%) | 8 | 2.1 (57.6) | 5.5 (53.2) | 8.5 $(43.9)^c$ | 7.9 (43.0) |

| Comparison | GMR (90% CI) | | |
|---|---|---|---|
| | $AUC_{0-inf}$ | $C_{max}$ | CL/F |
| Patients with Severe Renal Impairment/ Healthy Matched Control Subject | 1.83 (1.36, 2.46) | 1.42 (0.89, 2.27) | 0.55 (0.41, 0.74) |
| Patients with Moderate Renal Impairment/ Healthy Matched Control Subject | 2.06 (1.55, 2.74) | 1.68 (1.07, 2.63) | 0.49 (0.36, 0.65) |
| Patients with Mild Renal Impairment/ Healthy Matched Control Subject | 1.49 (1.11, 2.00) | 1.96 (1.23, 3.13) | 0.67 (0.50, 0.90) |

Concentration data converted from molar to ng/mL (molecular weight of vibegron = 444.5)
CI = confidence interval;
GMR = Geometric least-squares mean ratio between treatment populations
$^a$Median (minimum-maximum)
$^b$ Geometric mean (percent geometric coefficient of variation)
$^c$N = 7

3.4 Effect of Hepatic Impairment

The pharmacokinetics of a single dose of vibegron 100 mg were evaluated in 8 patients with moderate hepatic impairment (Child-Pugh Score of 7 to 9) and 8 healthy subjects matched for age, gender and BMI in a two-part, open-label, single-dose Phase 1 study. A statistical comparison of vibegron pharmacokinetic parameters is presented in Table 8. The $AUC_{0-inf}$ and $C_{max}$ GMRs (90% CI) for moderate hepatic impaired patients and healthy control subjects were 1.27 (0.96, 1.67) and 1.35 (0.88, 2.06), respectively suggesting that moderate hepatic impairment did not have a clinically important effect on the exposure of vibegron.

TABLE 8

Summary of Vibegron 100 mg Pharmacokinetic Parameters in Patients with Moderate Hepatic Impairment and Healthy Matched Control Subjects

| Pharmacokinetic Parameter | N | Geometric Least Squares Mean (95% CI) | | GMR | 90% CI |
|---|---|---|---|---|---|
| | | Moderate Hepatic Impairment | Healthy Matched Control Subjects | | |
| $AUC_{0-inf}$ (ng · hr/mL) | 8 | 1820 (1440, 2300) | 1440 (1140, 1810) | 1.27 | (0.96, 1.67) |
| $C_{max}$ (ng/mL) | 8 | 168 (118, 240) | 125 (87.6, 178) | 1.35 | (0.88, 2.06) |
| $T_{max}{}^a$ (hr) | 8 | 1.0 (0.5-3.0) | 1.5 (0.5-4.0) | | |
| Apparent terminal $t_{1/2}{}^b$ (hr) | 8 | 94.5 (8.88%) | 92.5 (9.37%) | | |
| CL/F$^b$ (L/hr) | 8 | 56.0 (31.2%) | 68.3 (36.0%) | | |
| Vz/F$^b$ (L) | 8 | 7640 (33.3%) | 9120 (30.7%) | | |

Concentration data converted from molar to ng/mL (molecular weight of vibegron = 444.5)
CI = confidence interval;
GMR = Geometric least-squares mean ratio between treatment populations
$^a$Median (minimum-maximum)
$^b$Geometric mean (percent geometric coefficient of variation)

3.5 Drug Interaction Studies

Four drug interaction studies evaluating vibegron in combination with six compounds were conducted. Table 9 summarizes the effect of ketoconazole, diltiazem or tolterodine on the pharmacokinetics of vibegron. Table 10 summarizes the effect of vibegron on the pharmacokinetics of digoxin, ethinyl estradiol, levonorgestrel or tolterodine.

Multiple doses of the strong CYP3A4/P-gp inhibitor, ketoconazole 200 mg and the moderate CYP3A4/P-gp inhibitor, diltiazem 240 mg were evaluated in combination with a single dose of vibegron 100 mg. GM vibegron $AUC_{0-inf}$ and $C_{max}$ increased 2.08-fold and 2.22 fold, respectively in the presence of multiple doses of 200 mg ketoconazole. GM vibegron $AUC_{0-inf}$ and $C_{max}$ increased 63% and 68%, respectively in the presence of multiple doses of 240 mg or 180 mg diltiazem. The GM $t_{1/2}$ was 75, 75.4, and 80.2 hours, respectively when vibegron was dosed alone, with diltiazem or with ketoconazole, respectively. This lack of increase of vibegron $t_{1/2}$ in the presence of ketoconazole or diltiazem suggests that the interaction occurred primarily in the absorption phase. However, these interactions are not expected to be clinically significant. Tolterodine ER 4 mg had no effect on the pharmacokinetics of vibegron.

Multiple doses of vibegron were evaluated in combination with the p-gp substrate, digoxin. The 90% CI for the $AUC_{0-inf}$ GMR of digoxin when co-administered with vibegron was contained within the 80-125% bioequivalence range suggesting that vibegron does not influence digoxin pharmacokinetics to a clinically significant degree. The pharmacokinetics of ethinyl estradiol (EE) and levonorgestrel (LNG), two common components of oral contraceptives were not altered by multiple doses of vibegron. The 90% CI for the GMR (EE/LNG+vibegron to EE/LNG alone) for the AUC and $C_{max}$ of EE were contained within 0.8 and 1.25. Although, LNG AUC and $C_{max}$ increased 18 to 21% in the presence of multiple doses of vibegron, these increases were not considered to be clinically significant. No clinically meaningful pharmacokinetic interaction occurs when vibegron 100 mg or 150 mg is co-administered with tolterodine ER 4 mg.

TABLE 9

Change in Pharmacokinetic Parameters of Vibegron in the Presence of Co-Administered Medication (Conmed)

| Conmed | Dose of Conmed (mg) | Dose of Vibegron (mg) | n | | Geometric Mean (95% CI) Vibegron alone | Conmed + Vibegron | Ratio (with/without conmed) of Vibegron Pharmacokinetic Parameters; No Effect = 1.00 GMR | (90% CI) |
|---|---|---|---|---|---|---|---|---|
| Ketoconazole | 200 mg every 12 hours | 100 mg single dose | 10 | AUC | 1370 (788, 2380) | 2850 (2100, 3870) | 2.08 | (1.66, 2.61) |
| | | | | $C_{max}$ | 113 (53.1, 241) | 251 (167, 379) | 2.22 | (1.50, 3.28) |
| Diltiazem ER | 240 mg QD | 100 mg single dose | 12 | AUC | 1330 (1130, 1570) | 2170 (1990, 2480) | 1.63 | (1.44, 1.85) |
| | | | | $C_{max}$ | 99.8 (73.8, 135) | 167 (129-217) | 1.68 | (1.41, 1.99) |
| Tolterodine ER | 4 mg QD | 100 mg QD | 24 | AUC | 1662 (1382, 2000) | 1791[a] (1533, 2094) | 1.08 | (0.94, 1.23) |
| | | | | $C_{max}$ | 158 (111, 224) | 163[a] (127, 209) | 1.03 | (0.74, 1.43) |
| | | 150 mg QD | 23 | AUC | 2783 (2409, 3218) | 3102[a] (2787, 3463) | 1.12 | (0.98, 1.27) |
| | | | | $C_{max}$ | 269 (210, 344) | 304[a] (260, 357) | 1.13 | (0.90, 1.42) |

[a] N = 12
Concentration data converted from molar to ng/mL (molecular weight of vibegron = 444.5)

TABLE 10

Drug Interactions: Change in Pharmacokinetic Parameters of Co-Administered Drug (Conmed) in the Presence of Vibegron

| Conmed | Dose of Conmed (mg) | Dose of Vibegron (mg) | n | | Geometric Mean (95% CI) of Conmed Conmed alone | Conmed + Vibegron | Ratio (with/without Vibegron) of Conmed Pharmacokinetic Parameters; No Effect = 1.00 GMR | (90% CI) |
|---|---|---|---|---|---|---|---|---|
| Digoxin | 0.25 mg single dose | 100 mg QD | 18 | AUC | 16600 (14600, 19200) | 1840[a] (16200, 21000) | 1.11 | (1.03, 1.19) |
| | | | | $C_{max}$ | 1160 (965, 1400) | 1410 (1170, 1700) | 1.21 | (1.09, 1.35) |
| Oral Contraceptive | 0.03 mg EE single dose | 100 mg QD | 18 | AUC | 810 (713, 920) | 838 (734, 958) | 1.04 | (1.00, 1.07) |
| | | | | $C_{max}$ | 71.9 (62.3, 82.9) | 68.8 (60.5, 78.3) | 0.96 | (0.90, 1.02) |
| | 0.15 mg LNG single dose | | | AUC | 31000 (26800, 35900) | 37600 (32300, 43700) | 1.21 | (1.13, 1.30) |
| | | | | $C_{max}$ | 2070 (1770, 2420) | 2440 (2100, 2840) | 1.18 | (1.09, 1.27) |

TABLE 10-continued

Drug Interactions: Change in Pharmacokinetic Parameters of
Co-Administered Drug (Conmed) in the Presence of Vibegron

| Conmed | Dose of Conmed (mg) | Dose of Vibegron (mg) | n | | Geometric Mean (95% CI) of Conmed | | Ratio (with/without Vibegron) of Conmed Pharmacokinetic Parameters; No Effect = 1.00 | |
|---|---|---|---|---|---|---|---|---|
| | | | | | Conmed alone | Conmed + Vibegron | GMR | (90% CI) |
| Tolterodine ER | 4 mg QD | 100 mg QD | 12 | AUC | 28.37 (15.03, 53.56) | 30.66 (16.24, 57.89) | 1.08 | (0.97, 1.21) |
| | | | | $C_{max}$ | 2.28 (1.32, 3.96) | 2.57 (1.48, 4.45) | 1.12 | (1.00, 1.26) |
| | | 150 mg QD | | AUC | 13.25$^a$ (7.39, 23.76) | 10.80 (6.02, 19.38) | 1.23 | (1.11, 1.35) |
| | | | | Cmax | 1.26$^a$ (0.66, 2.39) | 0.92 (0.48, 1.75) | 1.37 | (1.20, 1.57) |

GMR = Geometric Means Ratio; CI = confidence interval; EE = ethinyl estradiol; LNG = levonorgestrel Concentration data converted from molar to ng/mL (molecular weight of vibegron = 444.5)
$^a$N = 17
b. N = 11

3.6 Effect on QT Interval Prolongation

The effect of vibegron on QTc interval was evaluated in a single oral dose study. Fifty-two healthy subjects received a single dose of 400 mg vibegron, a single dose of vibegron 200 mg, a single dose of moxifloxacin 400 mg and a single dose of placebo to match vibegron.

The 400 mg dose of vibegron resulted in a maximum LS mean difference (90% CI) from placebo in QTcF of 4.60 (2.71, 6.48) msec at 1 hour post dose. A similar result was noted in QTcF after the 200 mg single dose where the maximum LS mean difference (90% CI) from placebo was 4.98 (3.07, 6.88) msec at 1 hour post dose. The upper limits of the 90% CIs of all of the mean differences fell below the target of 10 msec. (Table 11). A statistically significant effect of moxifloxacin on QTcF was observed.

The GM (CV %) $C_{max}$ and $AUC_{0-23.5hr}$ achieved following a single 200 mg dose were 366 (50.4) ng/mL and 2270 (37.3) ng·h/mL respectively. Vibegron $C_{max}$ was 1.63-fold the value obtained in elderly subjects receiving multiple doses of 100 mg in a double-blind, randomized, placebo-controlled, alternating (Panels A and B), multiple-period, single rising oral dose Phase 1 study, while the AUC was similar. The GM (CV %) $C_{max}$ and $AUC_{0-23.5hr}$ achieved following a single dose of 400 mg were 1020 (39.9) ng/mL and 6450 (34.0) ng·h/mL respectively. These $C_{max}$ and $AUC_{0-23.5hr}$ values are 4.55-fold and 2.89-fold the values obtained in elderly subjects receiving multiple doses of vibegron 100 mg.

Target PK exposures at both the 200 mg and 400 mg dose levels were achieved. The steady state $C_{max}$ and $AUC_{0-24hr}$ values achieved in elderly female subjects at the highest clinical dose of 100 mg were 278 ng/mL and 2620 ng·h/mL, respectively.

TABLE 11

Statistical Comparison for QTcF Change From Baseline Difference From Placebo (Vibegron − Placebo) by Treatment and Time Point Relative to the Administration of a Dose of 400 mg Vibegron, a Dose of 200 mg of Vibegron, and a Single Dose of Placebo to Vibegron

| | Single Dose of 400 mg Vibegron (msec) | | | Single Dose of 200 mg Vibegron (msec) | | | Single Dose of Placebo to Vibegron (msec) | | |
|---|---|---|---|---|---|---|---|---|---|
| Hour | N | LS Mean | 95% CI | N | LS Mean | 95% CI | N | LS Mean | 95% CI |
| 0.5 hour | 52 | 2.37 | (0.66, 4.07) | 50 | 1.90 | (0.16, 3.63) | 50 | −1.00 | (−2.74, 0.73) |
| 1 hour | 52 | 4.49 | (2.78, 6.19) | 50 | 4.87 | (3.13, 6.60) | 50 | −0.11 | (−1.84, 1.63) |
| 2 hour | 52 | 0.73 | (−0.97, 2.43) | 50 | 2.06 | (0.32, 3.79) | 50 | −0.08 | (−1.81, 1.65) |
| 3 hour | 52 | −0.30 | (−2.00, 1.41) | 50 | 1.14 | (−0.59, 2.88) | 50 | 0.74 | (−0.99, 2.47) |
| 4 hour | 52 | −2.53 | (−4.23, −0.82) | 50 | −0.40 | (−2.14, 1.33) | 50 | 0.43 | (−1.30, 2.17) |
| 6 hour | 52 | −8.33 | (−10.03, −6.62) | 50 | −6.89 | (−8.63, −5.16) | 50 | −5.63 | (−7.37, −3.90) |
| 8 hour | 52 | −11.60 | (−13.30, −9.89) | 50 | −9.59 | (−11.33, −7.86) | 50 | −8.36 | (−10.09, −6.62) |
| 10 hour | 52 | −10.29 | (−11.99, −8.58) | 50 | −8.82 | (−10.56, −7.09) | 50 | −6.15 | (−7.89, −4.42) |
| 12 hour | 52 | −7.10 | (−8.80, −5.39) | 50 | −6.82 | (−8.56, −5.09) | 50 | −3.10 | (−4.83, −1.37) |
| 23.5 hour | 52 | −2.87 | (−4.57, −1.17) | 50 | −2.15 | (−3.88, −0.41) | 50 | −2.53 | (−4.26, −0.79) |

| | Difference From Single Dose of Placebo to 400 mg Dose of Vibegron (msec) | | Difference From Single Dose of Placebo to 200 Dose of Vibegron (msec) | |
|---|---|---|---|---|
| Hour | LS Mean Difference | 90% CI $^a$ | LS Mean Difference | 90% CI $^a$ |
| 0.5 hour | 3.37 | (1.49, 5.25) | 2.90 | (1.00, 4.80) |
| 1 hour | 4.60 | (2.71, 6.48) | 4.98 | (3.07, 6.88) |
| 2 hour | 0.81 | (−1.07, 2.69) | 2.14 | (0.23, 4.04) |
| 3 hour | −1.04 | (−2.92, 0.85) | 0.40 | (−1.50, 2.30) |

TABLE 11-continued

Statistical Comparison for QTcF Change From Baseline Difference From Placebo (Vibegron − Placebo) by Treatment and Time Point Relative to the Administration of a Dose of 400 mg Vibegron, a Dose of 200 mg of Vibegron, and a Single Dose of Placebo to Vibegron

| 4 hour    | −2.96 | (−4.84, −1.08) | −0.83 | (−2.73, 1.07)  |
| 6 hour    | −2.70 | (−4.58, −0.81) | −1.26 | (−3.16, 0.64)  |
| 8 hour    | −3.24 | (−5.12, −1.36) | −1.24 | (−3.14, 0.66)  |
| 10 hour   | −4.14 | (−6.02, −2.25) | −2.67 | (−4.57, −0.77) |
| 12 hour   | −4.00 | (−5.88, −2.11) | −3.72 | (−5.63, −1.82) |
| 23.5 hour | −0.34 | (−2.22, 1.54)  | 0.38  | (−1.52, 2.28)  |

Abbreviations: LS mean, least square means, CI, confidence interval
400 mg vibegron: Single dose of 400 mg vibegron (8 × 50 mg tablets).
200 mg vibegron: Single dose of 200 mg vibegron (4 × 50 mg tablets vibegron + 4 × vibegron matching placebo tablets) Placebo: Single Dose of vibegron matching placebo (8 × vibegron matching placebo tablets).
QTcF results at baseline (arithmetic mean): Placebo = 407.38, 400 mg vibegron = 407.64, 200 mg vibegron = 406.75, Moxifloxacin = 407.77
[a] The two-sided 90% confidence intervals are equivalent to one-sided upper 95% confidence intervals.

Example 4

Clinical Efficacy Data

A randomized, double-blind, placebo- and active-controlled, parallel-group two-part Phase 2b study of vibegron in men and women with OAB (stratified as OAB wet and OAB dry) was completed. Part 1 was a dose-ranging study to assess the safety, tolerability, and efficacy of vibegron and proof of concept study for concomitant dosing of vibegron with tolterodine ER 4 mg. Approximately 980 subjects in Part 1 were equally randomized in a double-blind fashion to one of seven treatment arms: vibegron 3 mg, 15 mg, 50 mg, or 100 mg once daily for 8 weeks; tolterodine ER 4 mg once daily for 8 weeks; placebo once daily for 8 weeks; or vibegron 50 mg with tolterodine ER 4 mg for 4 weeks followed by vibegron 50 mg for 4 weeks. Part 2 was designed to continue to assess the safety and efficacy of concomitant dosing. In Part 2, 408 subjects were randomized in a double-blind fashion to one of four treatment arms in a 2:2:2:1 ratio: vibegron 100 mg, tolterodine ER 4 mg, vibegron 100 mg with tolterodine ER 4 mg, or placebo once daily for 4 weeks. Subjects in both Part 1 and Part 2 had the option of enrolling in a 1-year extension. Participants were required to keep a voiding diary, recording the occurrence of each strong urge, total incontinence, and urge incontinence episode. Efficacy data for Part 1 and Part 2 are summarized herein.

At baseline, subjects must have had an average number of micturitions ≥8 per diary day in the Voiding Diary. In addition, subjects in the OAB wet strata must have had an average number of urgency incontinence episodes ≥1 per diary day. Subjects in the OAB dry strata must have had an average number of urgency episodes ≥3 per diary day and an average of <1 urgency incontinence episodes per diary day. The total number of urgency incontinence episodes must have exceeded the total number of stress incontinence episodes for all subjects.

The primary objectives of this study were to assess the safety and tolerability of treatment with selected vibegron doses (alone or in combination with tolterodine) and to investigate dose-related reductions in average number of daily micturitions compared with placebo at Week 8.

In Part 1, statistically significant decreases in the average number of daily micturitions were observed in the vibegron 100 mg and 50 mg treatment groups as compared to the placebo group at Week 8. Statistically significant decreases from baseline as compared to placebo were also observed in the vibegron 100 mg and 50 mg treatment groups for secondary endpoints which included urgency incontinence and total incontinence (in subjects with OAB wet), and urgency episodes in all subjects. Statistically significant increases from baseline as compared to placebo were also observed for the secondary endpoint volume voided per micturition in the vibegron 15, 50 and 100 mg treatment groups. (Tables 12 and 13).

TABLE 12

Analysis of Change from Baseline In The Volume Voided (ML) Per Micturition at Week 8

| | | Difference from Placebo Week 8 | |
| --- | --- | --- | --- |
| Treatment | N | Difference in LS Means | p-value |
| Vibegron 3 mg | 144 | 15.99 | 0.032 |
| Vibegron 15 mg | 131 | 28.23 | <0.001 |
| Vibegron 50 mg | 146 | 29.05 | <0.001 |
| Vibegron 100 mg | 148 | 23.36 | 0.002 |
| Tolterodine ER 4 mg | 133 | 30.77 | <0.001 |

TABLE 13

Analysis of Change from Baseline in Average Daily Number Events at Week 8 - Constrained Longitudinal Data Analysis (cLDA) Modela (Full-Analysis-Set Population - Part 1 Base Study)

| | | | Daily Number of Events | | | | Change from Baseline | | Difference from Placebo Week 8 | |
| --- | --- | --- | --- | --- | --- | --- | --- | --- | --- | --- |
| | | | Baseline | | Week 8 | | Week 8 | | Difference in | |
| Event | Treatment | N | Mean | SD | Mean | SD | Mean | SD | LS Means[b] | p-value |
| Micturitions | Placebo | 141 | 10.86 | 2.84 | 9.77 | 2.51 | −1.09 | 2.17 | n/a | n/a |
| | Vibegron 3 mg | 144 | 10.93 | 2.35 | 9.35 | 2.43 | −1.56 | 1.97 | −0.46 | 0.056 |
| | Vibegron 15 mg | 132 | 11.32 | 3.48 | 9.53 | 2.85 | −1.71 | 2.22 | −0.45 | 0.064 |

TABLE 13-continued

Analysis of Change from Baseline in Average Daily Number Events at Week 8 - Constrained Longitudinal Data Analysis (cLDA) Modela (Full-Analysis-Set Population - Part 1 Base Study)

| Event | Treatment | N | Daily Number of Events Baseline Mean | Daily Number of Events Baseline SD | Daily Number of Events Week 8 Mean | Daily Number of Events Week 8 SD | Change from Baseline Week 8 Mean | Change from Baseline Week 8 SD | Difference from Placebo Week 8 Difference in LS Means[b] | Difference from Placebo Week 8 p-value |
|---|---|---|---|---|---|---|---|---|---|---|
| | Vibegron 50 mg | 148 | 11.21 | 3.16 | 9.05 | 2.28 | −1.87 | 1.78 | −0.64 | 0.007 |
| | Vibegron 100 mg | 148 | 11.15 | 2.32 | 9.02 | 2.59 | −2.11 | 1.81 | −0.91 | <0.001 |
| | Tolterodine ER 4 mg | 134 | 11.00 | 2.17 | 9.24 | 2.11 | −1.73 | 2.02 | −0.54 | 0.026 |
| Urgency | Placebo | 118 | 3.11 | 2.68 | 1.71 | 2.50 | −1.34 | 1.77 | n/a | n/a |
| Incontinence | Vibegron 3 mg | 113 | 2.70 | 1.94 | 1.21 | 1.68 | −1.38 | 1.38 | −0.28 | 0.167 |
| Episodes[c] | Vibegron 15 mg | 111 | 2.94 | 2.23 | 1.12 | 2.06 | −1.81 | 1.60 | −0.57 | 0.005 |
| | Vibegron 50 mg | 121 | 2.81 | 2.06 | 0.86 | 1.16 | −1.90 | 1.75 | −0.72 | <0.001 |
| | Vibegron 100 mg | 122 | 2.96 | 2.42 | 0.84 | 1.74 | −2.05 | 1.99 | −0.71 | <0.001 |
| | Tolterodine ER 4 mg | 100 | 2.80 | 2.13 | 1.15 | 2.18 | −1.67 | 1.55 | −0.46 | 0.030 |
| Total | Placebo | 118 | 3.61 | 3.26 | 1.88 | 2.68 | −1.68 | 2.01 | n/a | n/a |
| Incontinence | Vibegron 3 mg | 113 | 3.05 | 2.11 | 1.38 | 1.75 | −1.56 | 1.55 | −0.18 | 0.401 |
| Episodes[c] | Vibegron 15 mg | 111 | 3.32 | 2.44 | 1.31 | 2.26 | −1.99 | 1.64 | −0.48 | 0.029 |
| | Vibegron 50 mg | 121 | 3.10 | 2.26 | 1.02 | 1.40 | −2.02 | 1.82 | −0.60 | 0.005 |
| | Vibegron 100 mg | 122 | 3.43 | 2.83 | 1.12 | 2.08 | −2.26 | 2.41 | −0.58 | 0.007 |
| | Tolterodine ER 4 mg | 100 | 3.08 | 2.39 | 1.32 | 2.38 | −1.80 | 1.47 | −0.34 | 0.140 |
| Urgency | Placebo | 141 | 6.52 | 4.37 | 4.99 | 3.77 | −1.57 | 3.28 | n/a | n/a |
| Episodes | Vibegron 3 mg | 144 | 6.49 | 3.66 | 4.68 | 4.16 | −1.69 | 2.65 | −0.18 | 0.598 |
| | Vibegron 15 mg | 132 | 6.93 | 4.69 | 4.42 | 4.40 | −2.35 | 2.50 | −0.67 | 0.052 |
| | Vibegron 50 mg | 148 | 6.43 | 4.22 | 3.71 | 3.76 | −2.36 | 2.35 | −0.76 | 0.024 |
| | Vibegron 100 mg | 148 | 7.34 | 4.14 | 4.22 | 4.36 | −2.98 | 2.84 | −1.24 | <0.001 |
| | Tolterodine ER 4 mg | 134 | 6.39 | 3.78 | 3.91 | 3.65 | −2.52 | 2.73 | −0.94 | 0.007 | aConstrained longitudinal data analysis model includes terms for time, region and interaction of time by treatment.
[b]Negative mean treatment differences are in favor of former treatments in comparison.
[c]Only in OAB Wet subjects.

A double-blind, randomized, placebo controlled, multi-center, Phase 3 study designed to evaluate the safety and efficacy of vibegron in males and females with OAB was completed. Upon completion of the placebo Run-in period, 1,232 patients were randomized to receive blinded study treatment for 12 weeks including: vibegron 50 mg (N=370), vibegron 100 mg (N=369), placebo (N=369), or imidafenacin 0.2 mg (comparator; N=117). The results demonstrate that once daily vibegron produced statistically significant reductions in efficacy parameters including: micturitions, UUI episodes, total incontinence episodes, and urgency episodes (Table 14).

TABLE 14

Analysis of Change from Baseline in Average Daily Number Events at Week 12 - Constrained Longitudinal Data Analysis (cLDA) Modela

| Event | 50 mg Dose | 100 mg Dose |
|---|---|---|
| Micturitions | −0.86 (−1.12, −0.60) p < 0.0001 | −0.81 (−1.07, −0.55) p < 0.0001 |
| Urge Urinary Incontinence Episodes | −0.27 (−0.44, −0.10) p = 0.0015 | −0.39 (−0.55, −0.22) p < 0.0001 |
| Total Incontinence Episodes | −0.30 (−0.49, −0.12) p = 0.0015 | −0.43 (−0.61, −0.24) p < 0.0001 |
| Urgency Episodes | −0.51 (−0.76, −0.25) p = 0.0001 | −0.67 (−0.93, −0.42) p < 0.0001 |
| Volume Voided (mL) | 25.76 (20.02, 31.46) p < 0.0001 | 22.16 (16.44, 27.89) p < 0.0001 | aResults presented as least squares mean placebo adjusted change from baseline (95% confidence interval [CI]), p-value.

Example 5

Safety Data 5.1 Phase I Safety Data

Safety data from 16 Phase 1 studies, which include 15 completed Phase 1 studies and 1 study that was terminated early (this study was terminated for reasons unrelated to efficacy or safety) was collected. In the Phase 1 program, a total of 466 subjects received at least one dose of vibegron; 238 subjects received single doses ranging from 2 to 600 mg and 238 subjects received multiple doses ranging from 25 to 400 mg for up to 28 days. Across the Phase 1 program, vibegron has been generally well tolerated. There were no treatment-emergent serious adverse events (SAEs) or deaths reported, and the majority of adverse events (AEs) were transient and mild or moderate in intensity.

In Phase 1 studies, there were isolated occurrences of orthostatic hypotension (decrease in systolic blood pressure >20 mmHg and/or decrease in diastolic blood pressure >10 mmHg), with or without symptoms (e.g., lightheadedness, dizziness, presyncope). The incidence of orthostatic AEs following co-administration of vibegron 100 mg or 150 mg and tolterodine ER 4 mg was similar to the incidence of these AEs following administration of vibegron or tolterodine alone. At doses up to 100 mg in Phase 1 multiple dose studies, AEs such as postural dizziness, dizziness, presyncope, or syncope have not exhibited a clear dose-response relationship. However, postural dizziness appeared to increase at doses of 100 mg and above and the incidence of the AE "orthostatic hypotension with symptoms" has tended to be higher at vibegron doses >200 mg. There were no occurrences of orthostatic AEs when vibegron 100 mg was coadministered to subjects with essential hypertension who were on a stable regimen of either metoprolol (a representative beta-blocker), or amlodipine (a representative vasodilator).

Review of preliminary Phase 1 safety data suggest no clinically meaningful changes in laboratory safety parameters (chemistry, hematology and urinalyses) or ECG parameters, including PR, QRS and QTc intervals. A thorough QT study has been completed, which found no clinically meaningful effect on QTc or blood pressure 5.2 Phase II Safety Data Phase 2 safety data from a single Phase 2B study that has completed in which 933 subjects received at least one dose of vibegron was collected. Subjects received vibegron doses ranging from 3 to 100 mg for up to 8 weeks during the main study (alone or in combination with tolterodine). Of those completing the parent study, 605 subjects received doses of vibegron 50 mg (alone) or vibegron 100 mg (alone or in combination with tolterodine 4 mg) for up to 52 weeks during an extension study. A placebo group was included in the main study, and a group that received tolterodine monotherapy was included in the main study and in the extension. There were no deaths reported during the study. Vibegron was generally well tolerated. No meaningful differences in the overall incidence or severity of AEs or drug-related AEs were observed among the treatment groups compared to placebo.

Adverse events were reported in 607 (43.6%) of the 1393 allocated subjects in the main study. The proportion of subjects with one or more AEs in the vibegron 50 mg and vibegron 100 mg treatment groups was similar to placebo (see Table 14). A higher proportion of subjects reported one or more AEs in the vibegron 15 mg and vibegron 50 mg+tolterodine 4 mg treatment groups compared to placebo. The most frequently reported AEs were dry mouth, headache, urinary tract infections (UTI), and nasopharyngitis. The incidence of dry mouth was higher in groups that received tolterodine (alone or with vibegron) compared to the placebo or vibegron monotherapy groups.

There were 221 subjects with drug-related AEs, with the lowest incidence of drug-related AEs reported in the vibegron 100 mg treatment group. The proportion of subjects with drug-related AEs was similar in the vibegron monotherapy groups compared to placebo and only slightly higher in the concomitant treatment groups compared to placebo or either monotherapy. The proportion of subjects who discontinued due to a drug-related AE was low and similar across all treatment groups.

There were a total of 9 SAEs reported in 8 subjects and occurred across the treatment groups (2 placebo; 1 vibegron 3 mg; 1 vibegron 50 mg; 3 tolterodine 4 mg; 1 vibegron 50 mg+tolterodine 4 mg). The reported SAEs were atrial fibrillation, anaphylactic reaction, lung adenocarcinoma stage IV, chronic obstructive pulmonary disease, hypertension, overdose, foot fracture, and in one subject both gastroesphageal reflux disease and dizziness occurred after a pan endoscopic procedure that prolonged hospitalization. No specific AE term was reported in more than 1 subject. All SAEs were considered unrelated to study drug by the investigator.

During the 52-week extension, no meaningful differences in overall incidences of adverse events or serious adverse events were observed among the treatment groups.

Adverse events were reported in 531 (62.8%) of the 845 subjects. The proportion of subjects with one or more AEs was similar across all treatment groups. The most frequently reported adverse events were UTI, nasopharyngitis, upper respiratory tract infection, and dry mouth. The incidence of dry mouth was higher in the tolterodine ER 4 mg treatment group compared to the other treatment groups. The incidence of constipation was higher in the concomitant treatment group compared to the monotherapy treatment groups.

The proportion of subjects with drug-related AEs was slightly higher for tolterodine ER 4 mg and the concomitant dose arm compared to the vibegron 50 mg and 100 mg treatment arms. The proportion of subjects who discontinued due to an AE or a drug-related AE was higher for tolterodine ER 4 mg compared to the other treatment groups. There were total of 46 SAEs reported in 41 subjects during the extension. An overall higher incidence rate was reported in the tolterodine ER 4 mg and vibegron 50 mg treatment groups compared to the vibegron 100 mg treatment group. There was one drug-related SAE of ileus paralytic reported in the tolterodine ER 4 mg treatment group; the subject was discontinued due to this AE.

Table 15 below summarizes adverse events commonly seen in the vibegron Phase 2 program in patients with overactive bladder.

TABLE 15

Adverse Events in ≥2% Subjects in Phase 2 Study (First 12 weeks of Treatment)

| | Placebo N = 205 n (%) | Vibegron 3 mg N = 144 n (%) | Vibegron 15 mg N = 134 n (%) | Vibegron 50 mg N = 148 n (%) | Vibegron 100 mg N = 261 n (%) | Tolterodine ER 4 mg N = 257 n (%) | Vibegron 100 mg + tolterodine ER 4 mg N = 110 n (%) | Vibegron 50 mg + Tolterodine ER 4 mg/ Vibegron 50 mg N = 134 n (%) | Total N = 1,393 n (%) |
|---|---|---|---|---|---|---|---|---|---|
| ≥1 AE | 88 (42.9) | 55 (38.2) | 70 (52.2) | 62 (41.9) | 107 (41.0) | 116 (45.1) | 40 (36.4) | 69 (51.5) | |
| Serious AE | 2 (1.0) | 1 (0.7) | 0 | 1 (0.7) | 0 | 3 (1.2) | 0 | 1 (0.7) | |
| Drug-related AE | 30 (14.6) | 21 (14.6) | 23 (17.2) | 23 (15.5) | 31 (11.9) | 42 (16.3) | 21 (19.1) | 30 (14.6) | |
| Discontinuation due to AE | 5 (2.4) | 3 (2.1) | 4 (3.0) | 2 (1.4) | 6 (2.3) | 4 (1.6) | 2 (1.8) | 3 (2.2) | |
| Discontinuation due to drug-related AE | 3 (1.5) | 2 (1.4) | 4 (3.0) | 0 | 3 (1.1) | 0 | 1 (0.9) | 2 (1.5) | |
| SOC/Preferred Term Eye disorders | | | | | | | | | |
| Dry eye | 10 (4.9) | 2 (1.4) | 4 (3.0) | 2 (1.4) | 4 (1.5) | 10 (3.9) | 3 (2.7) | 2 (1.5) | 18 (1.3) |
| Gastrointestinal disorders | | | | | | | | | |
| Constipation | 5 (2.4) | 5 (3.5) | 6 (4.5) | 6 (4.1) | 2 (0.8) | 5 (1.9) | 4 (3.6) | 6 (4.5) | 39 (2.8) |
| Diarrhea | 5 (2.4) | 4 (2.8) | 2 (1.5) | 1 (0.7) | 5 (1.9) | 9 (3.5) | 1 (0.9) | 6 (4.5) | 33 (2.4) |
| Dry mouth | 6 (2.9) | 5 (3.5) | 6 (4.5) | 7 (4.7) | 4 (1.5) | 22 (8.6) | 13 (11.8) | 11 (8.2) | 74 (5.3) |
| Nausea | 3 (1.5) | 2 (1.4) | 2 (1.5) | 3 (2.0) | 3 (1.1) | 6 (2.3) | 0 (0.0) | 2 (1.5) | 21 (1.5) |

TABLE 15-continued

Adverse Events in ≥2% Subjects in Phase 2 Study (First 12 weeks of Treatment)

| | Placebo N = 205 n (%) | Vibegron 3 mg N = 144 n (%) | Vibegron 15 mg N = 134 n (%) | Vibegron 50 mg N = 148 n (%) | Vibegron 100 mg N = 261 n (%) | Tolterodine ER 4 mg N = 257 n (%) | Vibegron 100 mg + tolterodine ER 4 mg N = 110 n (%) | Vibegron 50 mg + Tolterodine ER 4 mg/ Vibegron 50 mg N = 134 n (%) | Total N = 1,393 n (%) |
|---|---|---|---|---|---|---|---|---|---|
| *General disorders and administration site conditions* | | | | | | | | | |
| Fatigue | 1 (0.5) | 4 (2.8) | 6 (4.5) | 5 (3.4) | 2 (0.8) | 6 (2.3) | 2 (1.8) | 2 (1.5) | 28 (2.0) |
| *Infections and infestations* | | | | | | | | | |
| Nasopharyngitis | 14 (6.8) | 3 (2.1) | 7 (5.2) | 8 (5.4) | 10 (3.8) | 4 (1.6) | 2 (1.8) | 3 (2.2) | 51 (3.7) |
| Sinusitis | 2 (1.0) | 0 0 | 2 (1.5) | 1 (0.7) | 0 0 | 1 (0.4) | 0 (0.0) | 4 (3.0) | 10 (0.7) |
| Urinary tract infection | 7 (3.4) | 5 (3.5) | 5 (3.7) | 8 (5.4) | 8 (3.1) | 12 (4.7) | 5 (4.5) | 7 (5.2) | 57 (4.1) |
| *Injury, poisoning and procedural complications* | | | | | | | | | |
| Accidental overdose | 2 (1.0) | 3 (2.1) | 6 (4.5) | 4 (2.7) | 11 (4.2) | 6 (2.3) | 1 (0.9) | 2 (1.5) | 35 (2.5) |
| *Investigations* | | | | | | | | | |
| Alanine aminotransferase increased | 0 (0.0) | 0 (0.0) | 0 (0.0) | 0 (0.0) | 0 (0.0) | 1 (0.4) | 0 (0.0) | 3 (2.2) | 4 (0.3) |
| Aspartate aminotransferase increased | 0 (0.0) | 0 (0.0) | 1 (0.7) | 0 (0.0) | 0 (0.0) | 0 (0.0) | 0 (0.0) | 3 (2.2) | 4 (0.3) |
| *Musculoskeletal and connective tissue disorders* | | | | | | | | | |
| Arthralgia | 2 (1.0) | 0 0 | 2 (1.5) | 3 (2.0) | 0 (0.0) | 3 (1.2) | 1 (0.9) | 0 (0.0) | 11 (0.8) |
| Osteoarthritis | 1 (0.5) | 2 (1.4) | 1 (0.7) | 4 (2.7) | 1 (0.4) | 0 (0.0) | 0 (0.0) | 0 (0.0) | 9 (0.6) |
| Pain in extremity | 0 0 | 2 (1.4) | 0 0 | 2 (1.4) | 1 (0.4) | 1 (0.4) | 3 (2.7) | 2 (1.5) | 11 (0.8) |
| *Nervous system disorders* | | | | | | | | | |
| Dizziness | 5 (2.4) | 1 (0.7) | 6 (4.5) | 3 (2.0) | 7 (2.7) | 5 (1.9) | 3 (2.7) | 1 (0.7) | 31 (2.0) |
| Headache | 9 (4.4) | 3 (2.1) | 6 (4.5) | 6 (4.1) | 12 (4.6) | 9 (3.5) | 7 (6.4) | 6 (4.5) | 58 (4.0) |
| *Renal and urinary disorders* | | | | | | | | | |
| Dysuria | 1 (0.5) | 0 (0.0) | 0 (0.0) | 1 (0.7) | 0 (0.0) | 3 (1.2) | 3 (2.7) | 0 (0.0) | 8 (0.6) |

Serious adverse events observed during the first 12 weeks of treatment with vibegron monotherapy included lung adenocarcinoma stage IV (n=1) and chronic obstructive pulmonary disease (n=1); an SAE of overdose was reported in the vibegron-tolterodine combination arm. During the Phase 2 extension study, SAEs reported by 2 or more subjects receiving monotherapy included cerebrovascular accident (n=2) and osteoarthritis (n=2). The only SAE reported in the vibegron-tolterodine combination arm was *borrelia* infection. SAEs potentially related to a change in heart rate or blood pressure (at any time during treatment) included: loss of consciousness after 8 weeks of vibegron that did not recur on rechallenge (n=1), and in the tolterodine monotherapy arm atrial fibrillation (n=1) and dizziness (n=1). The frequency of injuries was numerically higher in the tolterodine arm than with vibegron (2.1%, n=5, vs. 0.9%, n=4). Given the low incidence and lack of a pattern for SAEs, no serious event is considered expected for vibegron.

Potential risks that may be associated with vibegron treatment, based on nonclinical data and data available for similar compounds, include orthostatic hypotension and increased exposure (~2-fold) in patients taking concomitant strong P-gp inducers.

5.3 Cardiovascular Safety

The cardiovascular safety of vibegron has been evaluated in patients with OAB and healthy volunteers. In a randomized, placebo- and active comparator (tolterodine)-controlled, 2-part efficacy and safety study with 52-week extension, seven orthostatic related AEs (which included the adverse event terms of postural dizziness, presyncope, and orthostatic hypotension) occurred in 6 (0.4%) subjects. The events occurred in one subject each in the placebo group (0.5%), the vibegron 15 mg group (0.3%), and the vibegron 50 mg+tolterodine ER/vibegron 50 mg treatment group (0.8%), and in 3 subjects in the vibegron 100 mg group (1.1%). The events occurred at random times throughout the study and were judged by the investigator to be mild in severity. None led to discontinuation. The overall incidence of orthostatic symptoms was low.

Changes from baseline in BP and HR across treatment groups are shown in Table 16. For systolic blood pressure (SBP) and diastolic blood pressure (DBP), the mean changes at Week 1 and mean maximum changes over 8 weeks for 50 mg and 100 mg were comparable between placebo and vibegron, with differences of <1 mm Hg. Categorical changes in SBP and DBP also were similar between placebo and vibegron, with a slight increase at 100 mg in percent of vibegron subjects with a change from baseline in DBP >15 mmHg (1.3% 100 mg vs 0.5% placebo). No dose-dependent pattern was detectable for HR, as the mean maximum changes over 8 weeks were comparable to placebo (<2 bpm). Small differences in the percent of subjects exceeding categorical heart rate and blood pressure thresholds for vibegron were similar to those in the tolterodine arm.

TABLE 16

Vital Sign Changes from Baseline for Vibegron and Tolterodine by Dose
HR Change from Baseline

| Treatment | n | Mean (95% CI) (week 1) | n | Mean (95% CI) Maximum | ≥ 5 mm Hg n/N (%) | ≥ 10 bpm n/N (%) | ≥15 bpm n/N (%) |
|---|---|---|---|---|---|---|---|
| Placebo | 186 | 0.12 (−1.04, 1.28) | 200 | 5.08 (4.02, 6.13) | 17/188 (9.0) | 1/188 (0.5) | 0 |
| 3 mg | 141 | 0.36 (−0.90, 1.62) | 143 | 5.57 (4.25, 6.90) | 16/140 (11.4) | 5/140 (3.6) | 1/140 (0.7) |
| 15 mg | 126 | 0.35 (−1.15, 1.85) | 134 | 6.56 (5.20, 7.92) | 17/132 (12.9) | 4/132 (3.0) | 1/132 (0.8) |
| 50 mg | 140 | 0.29 (−0.88, 1.46) | 146 | 5.49 (4.28, 6.69) | 12/144 (8.3) | 4/144 (2.8) | 1/144 (0.7) |
| 100 mg | 237 | 0.35 (−0.69, 1.38) | 257 | 6.12 (5.10, 7.15) | 28/237 (11.8) | 7/237 (3.0) | 1/237 (0.4) |
| Tolterodine 4 mg | 246 | 0.68 (−0.31, 1.67) | 257 | 5.66 (4.69, 6.63) | 29/242 (12.0) | 11/242 (4.5) | 4/242 (1.7) |

SBP Change from Baseline

| Treatment | n | Mean (95% CI) (week 1) | n | Mean (95% CI) Maximum | ≥ 5 mm Hg n/N (%) | ≥ 10 mm Hg n/N (%) | ≥15 mm Hg n/N (%) |
|---|---|---|---|---|---|---|---|
| Placebo | 186 | −0.21 (−1.85, 1.43) | 200 | 7.84 (6.27, 9.40) | 24/188 (12.8) | 10/188 (5.3) | 3/188 (1.6) |
| 3 mg | 141 | −0.35 (−2.34, 1.65) | 143 | 7.14 (5.18, 9.10) | 21/140 (15.0) | 10/140 (7.1) | 4/140 (2.9) |
| 15 mg | 126 | −0.34 (−2.46, 1.78) | 134 | 8.93 (7.18, 10.67) | 22/132 (16.7) | 9/132 (6.8) | 1/132 (0.8) |
| 50 mg | 140 | −0.79 (−2.65, 1.08) | 146 | 7.01 (5.31, 8.70) | 24/144 (16.7) | 14/144 (9.7) | 3/144 (2.1) |
| 100 mg | 237 | −0.77 (−2.22, 0.68) | 257 | 6.51 (5.09, 7.93) | 28/237 (11.8) | 10/237 (4.2) | 3/237 (1.3) |
| Tolterodine 4 mg | 246 | 0.04 (−1.36, 1.43) | 257 | 7.29 (6.01, 8.57) | 41/242 (16.9) | 19/242 (7.9) | 7/242 (2.9) |

DBP Change from Baseline

| Treatment | n | Mean (95% CI) (week 1) | n | Mean (95% CI) Max | ≥ 5 mm Hg n/N (%) | ≥ 10 mmHg n/N (%) | ≥15 mm n/N Hg (%) |
|---|---|---|---|---|---|---|---|
| Placebo | 186 | 0.11 (−0.94, 1.17) | 200 | 4.89 (3.89, 5.89) | 18/188 (9.6) | 6/188 (3.2) | 1/188 (0.5) |
| 3 mg | 141 | −0.37 (−1.69, 0.95) | 143 | 5.03 (3.92, 6.15) | 14/140 (10.0) | 3/140 (2.1) | 1/140 (0.7) |
| 15 mg | 126 | 0.03 (−1.52, 1.59) | 134 | 6.37 (5.20, 7.53) | 15/132 (11.4) | 3/132 (2.3) | 1/132 (0.8) |
| 50 mg | 140 | −0.70 (−2.07, 0.67) | 146 | 4.19 (3.10, 5.29) | 11/144 (7.6) | 5/144 (3.5) | 1/144 (0.7) |
| 100 mg | 237 | −0.69 (−1.72, 0.34) | 257 | 4.80 (3.88, 5.72) | 31/237 (13.1) | 8/237 (3.4) | 3/237 (1.3) |
| Tolterodine 4 mg | 246 | −0.12 (−1.10, 0.86) | 257 | 5.19 (4.26, 6.13) | 30/242 (12.4) | 13/242 (5.4) | 3/242 (1.2) |

Mean maximum is from week 1 to 8.
Counts based on 3 Consecutive Post-Baseline Visits.

More intensive assessments of heart rate and blood pressure were performed in healthy volunteers in several Phase 1 studies. A 6-part, double-blinded, randomized, placebo-controlled study to assess the safety, tolerability and multiple-dose PK of vibegron in healthy subjects that included specific analyses for heart rate. Doses ranged from 25 to 400 mg once daily for 7 to 28 days depending on the cohort. Least squares mean and 90% confidence intervals of maximum change from baseline in moving average of heart rate over 4 hours postdose (MA4 HR) are presented in Table 17. Effects on heart rate were dose dependent and the 100 mg dose demonstrated a <1 bpm difference from placebo.

TABLE 17

Maximum MA4 HR and Difference between
Vibegron and Placebo at Day 14

| Panel | Dose (mg) | N[a] | $_{Maximum}$MA4 HR[b] | Difference from Placebo[c] |
|---|---|---|---|---|
| All | Placebo | 14 | 3.07 (0.26, 5.88) | |
| A | 25 | 5 | 1.47 (−3.24, 6.17) | −1.60 (−7.09, 3.88) |
| B | 50 | 6 | 1.50 (−2.79, 5.79) | −1.57 (−6.70, 3.56) |
| C | 100 | 6 | 3.28 (−1.02, 7.57) | 0.21 (−4.93, 5.34) |
| D | 150 | 6 | 3.17 (−1.13, 7.46) | 0.10 (−5.04, 5.23) |
| G | 200 | 5 | 5.67 (0.96, 10.37) | 2.60 (−2.89, 8.08) |

TABLE 17-continued

Maximum MA4 HR and Difference between
Vibegron and Placebo at Day 14

| Panel | Dose (mg) | N[a] | $_{Maximum}$MA4 HR[b] | Difference from Placebo[c] |
|---|---|---|---|---|
| H | 300 | 6 | 9.06 (4.76, 13.35) | 5.98 (0.85, 11.12) |
| I | 400 | 6 | 10.33 (6.04, 14.63) | 7.26 (2.13, 12.39) |

[a]One subject each in panels A and G discontinued and had no available data at day 14
[b]Least-square mean and corresponding 90% confidence interval
[c]Difference of least squares (active − placebo) and corresponding 90% confidence interval calculated from the linear fixed effects model Cardiovascular safety was also assessed in healthy volunteers in the thorough QT study following single doses of 200 and 400 mg, which approximate vibegron steady-state exposures at 100 mg and 200 mg, respectively. Mean maximum effects on blood pressure and RR interval were reduced with the lower dose as shown in Table 18. Using a log-log regression analysis from multiple-dose vibegron exposures (from three Phase 1 studies), the calculated mean±standard deviation $C_{max}$ and AUC from a 75 mg dose were 120±74.7 ng/mL and 1140±476 ng·h/mL, respectively. These estimations represent a $C_{max}$ and AUC that are approximately 3.3-fold and 2-fold lower, respectively, than the 200 mg single dose and 9.2-fold and 6-fold lower, respectively, than the 400 mg single dose.

TABLE 18

Single-Dose Pharmacokinetic Parameters and Mean Placebo-Corrected Change from Baseline RR interval and Blood Pressure

| Dose (mg) | Mean ± SD $C_{max}$ (ng/mL) | Mean ± SD AUC (ng · h/mL) | Maximum Mean Placebo Corrected Change from Baseline RR interval (90% CI) (msec) | Maximum Mean Placebo Corrected Change from Baseline Systolic BP (90% CI) (mmHg) | Maximum Mean Placebo Corrected Change from Baseline Diastolic BP (90% CI) (mmHg) |
|---|---|---|---|---|---|
| Vibegron 400 | 1100 ± 436 | 6800 ± 2300 | −162.45 (−184.24, −140.65) | 3.97 (2.12, 5.81) | 3.99 (2.62, 5.36) |
| Vibegron 200 | 406 ± 180 | 2430 ± 974 | −84.36 (−106.37, −62.35) | 2.20 (0.34, 4.06) | 2.42 (1.04, 3.81) |

Example 6

Dose Selection 6.1 Dose Comparison Efficacy

The Phase 2 study discussed in Example 4 demonstrated a dose-dependent effect on micturitions as seen in Table 19. Conversely, a dose dependent effect on urge incontinence or total incontinence was not observed. These data reveal a relatively shallow dose-response relationship between 50 and 100 mg once daily. Since vibegron efficacy begins to plateau from 50 to 100 mg, 75 mg captures a majority of the efficacy achieved with 100 mg.

TABLE 19

Efficacy of Vibegron 50 mg and 100 mg in Phase 2 Study

| Parameter | 50 mg - Placebo | 100 mg - Placebo | 100 mg − 50 mg |
|---|---|---|---|
| Micturitions[a] | −0.64 | −0.91 | −0.27 |
| Urgency incontinence[b] | −0.72 | −0.71 | 0.01 |
| Total incontinence[b] | −0.60 | −0.58 | 0.02 |
| Urgency Episodes[b] | −0.76 | −1.24 | −0.48 |
| Volume voided[c] (ml) | 29.1 | 23.4 | −5.69 |

Data reported as difference in LS means
[a]change from baseline in average number of micturitions at week 8
[b]change from baseline in average number of episodes at week 8
[c]change from baseline in average volume per void over one diary day at week 8

6.2 Mitigating Side Effects

Vibegron demonstrates greater than a dose proportional increase in exposures. Surprisingly, an increase in dose from 50 to 100 mg results in an approximate 3-fold increase in $C_{max}$, the PK parameter considered most closely associated with cardiovascular effects. In order to contextualize PK parameters of a 75 mg dose, dose-$C_{max}$ and dose-AUC models were created using data from Phase 1 studies. Based on simulations, it was found that a vibegron dose of 75 mg avoids approximately 29% of the exposures observed with a 100 mg dose, subsequently reducing the upper range of exposures that would be achieved with a 100 mg dose. This reduction in outlier $C_{max}$ values reduces the potential for clinically relevant cardiovascular effects.

In Phase 1 multiple dose studies, at doses up to 100 mg, adverse events such as postural dizziness, dizziness, presyncope, syncope did not exhibit a clear dose-response relationship. However, postural dizziness appeared to increase at doses ≥100 mg and the incidence of the adverse event "orthostatic hypotension with symptoms" was higher at vibegron doses greater than 150 mg. The risk of these dose-related adverse events can be disproportionally reduced by decreasing the dose from 100 mg to 75 mg, as a 25% reduction in dose produces an approximate 40% reduction in $C_{max}$ (120 ng/mL with 75 mg vs. 206 ng/mL with 100 mg). Without wishing to be bound by theory, the greater than dose-proportional increase in bioavailability with increasing dose may be due to saturable P-glycoprotein (P-gp)-mediated efflux in the gut.

A lower exposure with the 75 mg dose compared to a 100 mg dose disproportionally reduces the risk of adverse events in special populations as well. Subjects with moderate renal impairment had a mean increase in AUC of 1.6-fold compared to subjects with normal renal function whereas subjects receiving a potent CYP3A/P-gp inhibitor had an approximate 2-fold higher exposure. Assuming a 2 fold increase in $C_{max}$ of a 75 mg dose, the probability of these special populations achieving a vibegron $C_{max}$ greater than those observed with 100 mg is 15% (see FIG. 1). Minimizing exposures of subjects who fall at the extremes is important for elderly and females who demonstrated approximately a 50-70% higher $C_{max}$ than healthy young males.

Example 7

Pharmacokinetic Data for 75 mg Dose

A pharmacokinetic study evaluating the drug interaction of vibegron and rifampin was completed. All subjects were healthy adults. A summary of the preliminary results is presented in Table 20. Subjects received a single dose of vibegron 75 mg on day 1, rifampin 600 mg QD on days 10-23, and a single dose of vibegron 75 mg on day 17 concomitantly with the rifampin dose. Administration of vibegron and rifampin were well tolerated in healthy male and female subjects. There were no severe TEAEs, SAEs or deaths reported during the study. Three of 20 subjects (15%) experienced an AE related to study drug, 2 headache and 1 constipation, all mild. No clinically significant changes or findings were observed in vital signs, ECGs or clinical laboratory assessments.

TABLE 20

Geometric Mean (% CV): Pharmacokinetic Parameters of Vibegron

| Pharmacokinetic Parameters | Regimens | |
|---|---|---|
| | Vibegron alone (N = 18) | Vibegron + Rifampin (N = 18) |
| $t_{max}^{a}$ (h) | 1.0 (0.5, 2.0) | 1.0 (0.5, 2.0) |
| $C_{max}$ (ng/mL) | 82.3 (43.2) | 153.9 (47.1) |
| $AUC_{0-t}$ (ng · h/mL) | 1160 (34.3) | 1210 (30.7) |
| $AUC_{0-\infty}$ (ng · h/mL) | 1310 (36.4) | 1310 (31.5) |
| $t_{1/2}$ (h) | 84.0 (15.0) | 74.2 (25.2) |

TABLE 20-continued

Geometric Mean (% CV): Pharmacokinetic Parameters of Vibegron

| Pharmacokinetic Parameters | Regimens | |
|---|---|---|
| | Vibegron alone (N = 18) | Vibegron + Rifampin (N = 18) |
| CL/F (L/hr) | 57.2 (39.7) | 57.3 (30.1) |
| V/F (L) | 6930 (48.6) | 6140 (47.0) |

[a]Median (minimum, maximum)

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents, patent applications, and other publications cited herein are fully incorporated by reference herein in their entirety.

What is claimed is:

1. A method of treating overactive bladder in a human subject in need thereof, the method comprising administering to the subject about 75 mg per day of vibegron or a pharmaceutically acceptable salt thereof.

2. The method of claim 1, wherein treating overactive bladder comprises treating one or more symptoms selected from urge urinary incontinence (UUI), urinary urgency, urinary frequency, nocturia, or a combination thereof.

3. The method of claim 1, wherein the overactive bladder comprises symptoms of urge urinary incontinence (UUI), urinary urgency, and urinary frequency.

4. The method of claim 3, wherein vibegron is administered once per day.

5. The method of claim 4, wherein vibegron is administered with a meal.

6. The method of claim 4, wherein vibegron is administered without a meal.

7. The method of claim 4, wherein vibegron is administered as a tablet.

8. The method of claim 7, wherein the tablet is crushed before administration.

9. The method of claim 1, wherein after administration vibegron is effective in treating overactive bladder in about 4 weeks, about 3 weeks, or about 2 weeks.

10. The method of claim 9, wherein after administration vibegron is effective in treating overactive bladder in about 2 weeks.

11. The method of claim 1, wherein the subject is a female.

12. The method of claim 1, wherein the subject is a male.

13. The method of claim 1, wherein the subject suffers from severe renal impairment.

14. The method of claim 1, wherein the subject suffers from moderate renal impairment.

15. The method of claim 1, wherein the subject is concomitantly receiving a CYP3A/P-glycoprotein inhibitor.

16. The method of claim 1, wherein the subject is concomitantly receiving a CYP2D6 substrate, a CYP2C9 substrate, a CYP3A inhibitor, a P-glycoprotein inhibitor, an oral contraceptive, or a combination thereof.

17. The method of claim 1, wherein a pharmaceutically acceptable salt of vibegron is administered.

18. The method of claim 1, wherein the subject experiences a mean change of systolic blood pressure from baseline over a treatment period, wherein the mean change is less than 1 mm/Hg from that of a subject taking a placebo.

19. The method of claim 18, wherein the treatment period is selected from the group consisting of about 2, 4, 6, 8, 12, and 52 weeks.

20. The method of claim 1, wherein the percent of subjects that experience a mean change of systolic blood pressure from baseline of ≥15 mm/Hg over a treatment period is about 1.3%.

21. The method of claim 1, wherein the subject experiences a mean change of diastolic blood pressure from baseline over a treatment period, wherein the mean change is less than 1 mm/Hg from that of a subject taking a placebo.

22. The method of claim 1, wherein the subject experiences a mean change of diastolic blood pressure from baseline of less than 5 mm/Hg over a treatment period.

23. The method of claim 1, wherein the subject experiences a change in average number of micturitions per 24 hours from baseline of from about −1.5 to about −2.1 over a treatment period.

24. The method of claim 1, wherein the subject experiences a difference from placebo in average number of micturitions per 24 hours of from about −0.4 to about −0.8 over a treatment period.

25. The method of claim 1, wherein the subject has an average of ≥1 urge urinary incontinence (UUI) episodes per day prior to treatment and experiences a change in average number of UUI episodes from baseline of from about −1.8 to about −2.3 over a treatment period.

26. The method of claim 1, wherein the subject has an average of >1 urge urinary incontinence (UUI) episodes per day prior to treatment and experiences a difference from placebo in average number of UUI episodes of from about −0.3 to about −0.9 over a treatment period.

27. The method of claim 1, wherein the subject experiences a change in average number of urgency episodes from baseline of from about −2.3 to about −3.0 over a treatment period.

28. The method of claim 1, wherein the subject experiences a change in average number of total incontinence episodes from baseline of from about −2.0 to about −2.3 over a treatment period.

29. The method of claim 1, wherein the subject experiences a difference from placebo in increased volume voided per micturition of from about 20 mL to about 28 mL over a treatment period.

30. The method of claim 1, wherein treating overactive bladder comprises treating one or more symptoms of nocturia.

31. A method of treating overactive bladder in a human subject in need thereof, the method comprising administering to the subject about 75 mg of vibegron per day, wherein the pharmacokinetic profile of vibegron following a single dose has an area under the curve (AUC) of about 1140 ng-hr/mL±476 ng-hr/mL.

32. The method of claim 31, wherein the subject suffers from severe renal impairment.

33. The method of claim 31, wherein the subject suffers from moderate renal impairment.

34. The method of claim 31, wherein the subject is concomitantly receiving a CYP3A/P-glycoprotein inhibitor.

35. The method of claim 31, wherein the subject is concomitantly receiving a CYP2D6 substrate, a CYP2C9 substrate, a CYP3A inhibitor, a P-glycoprotein inhibitor, an oral contraceptive, or a combination thereof.

36. The method of claim 31, wherein the subject experiences a mean change of diastolic blood pressure from baseline of less than 5 mm/Hg over a treatment period.

37. A method of treating overactive bladder in a human subject in need thereof, the method comprising administering to the subject about 75 mg of vibegron per day, wherein the pharmacokinetic profile of vibegron following a single dose has a $C_{max}$ of about 120 ng/mL±74.7 ng/mL.

38. The method of claim 37, wherein the subject suffers from severe renal impairment.

39. The method of claim 37, wherein the subject suffers from moderate renal impairment.

40. The method of claim 37, wherein the subject is concomitantly receiving a CYP3A/P-glycoprotein inhibitor.

41. The method of claim 37, wherein the subject is concomitantly receiving a CYP2D6 substrate, a CYP2C9 substrate, a CYP3A inhibitor, a P-glycoprotein inhibitor, an oral contraceptive, or a combination thereof.

42. The method of claim 37, wherein the subject experiences a mean change of diastolic blood pressure from baseline of less than 5 mm/Hg over a treatment period.

43. A method of reducing the average number of micturitions per 24 hours in a human subject, the method comprising administering to the subject about 75 mg of vibegron per day, wherein the vibegron reduces the average number of micturitions to treat overactive bladder.

44. The method of claim 43, wherein the average number of micturitions per 24 hours is reduced from baseline by about −1.5 to about −2.1 over a treatment period.

45. The method of claim 43, wherein the difference from placebo in average number of micturitions per 24 hours is about −0.4 to about −0.8 over a treatment period.

46. A method of reducing the average number of UUI episodes per day in a human subject, the method comprising administering to the subject about 75 mg of vibegron per day, wherein the vibegron reduces the average number of UUI episodes to treat overactive bladder.

47. The method of claim 46, wherein the average number of UUI episodes per day is reduced from baseline by about −1.8 to about −2.3 over a treatment period.

48. The method of claim 46, wherein the difference from placebo in average number of UUI episodes is from about −0.3 to about −0.9 over a treatment period.

49. A method of reducing the average number of urgency episodes per day in a human subject, the method comprising administering to the subject about 75 mg of vibegron per day, wherein the vibegron reduces the average number of urgency episodes to treat overactive bladder.

50. The method of claim 49, wherein the average number of urgency episodes per day is reduced from baseline by at least 50% over a treatment period.

51. A method of reducing the average number of total incontinence episodes per day in a human subject, the method comprising administering to the subject about 75 mg of vibegron per day, wherein the vibegron reduces the average number of total incontinence episodes to treat overactive bladder.

52. The method of claim 51, wherein the average number of total incontinence episodes per day is reduced from baseline by about −2.0 to about −2.3 over a treatment period.

53. A method of increasing the volume voided (mL) per micturition in a human subject, the method comprising administering to the subject about 75 mg of vibegron per day, wherein the vibegron increases volume voided per micturition to treat overactive bladder.

54. The method of claim 53, wherein the increase in volume voided (mL) per micturition is increased from placebo from about 20 mL to about 28 mL over a treatment period.

* * * * *